(12) United States Patent
Connor et al.

(10) Patent No.: US 8,071,542 B2
(45) Date of Patent: Dec. 6, 2011

(54) USE OF FERRITIN TO TREAT IRON DEFICIENCY DISORDERS

(75) Inventors: James R. Connor, Hershey, PA (US); Ralph Lauren Keil, Palmyra, PA (US)

(73) Assignee: Chyna, LLC, Hershey, PA (US)

( * ) Notice: Subject to any disclaimer, the term of this patent is extended or adjusted under 35 U.S.C. 154(b) by 201 days.

(21) Appl. No.: 12/021,922

(22) Filed: Jan. 29, 2008

(65) Prior Publication Data
US 2009/0142360 A1 Jun. 4, 2009

Related U.S. Application Data

(60) Provisional application No. 60/886,972, filed on Jan. 29, 2007, provisional application No. 60/984,007, filed on Oct. 31, 2007.

(51) Int. Cl.
*A61K 38/00* (2006.01)
(52) U.S. Cl. .......................... 514/5.4; 514/1.2; 514/17.7
(58) Field of Classification Search .................... None
See application file for complete search history.

(56) References Cited

U.S. PATENT DOCUMENTS

| | | |
|---|---|---|
| 2004/0186048 A1 | 9/2004 | Broyles et al. |
| 2006/0116349 A1 | 6/2006 | Helenek et al. |
| 2007/0160658 A1 | 7/2007 | Connor et al. |

OTHER PUBLICATIONS

Fisher et al., Am J Physiol Cell Physiol 293: C641-C649, 2007.*
University of Maryland Medicine web publication, "Blood Diseases: Iron Deficiency Anemia", author unknown, published 2003, accessed from http://web.archive.org/web/20030803190356/www.umm.edu/blood/aneiron.htm Apr. 1, 2010.*
Mahoney et al., "Potential of the Rat as a Model for Predicting Iron Bioavailability for Humans", Nutrition Research, vol. 4, pp. 913-922, 1984.
Chang et al., "Recovery from iron deficiency in rats by the intake of recombinant yeast producing human H- ferritin", Nutrition 21 (2005) 520-524.
Seo et at., "Enhanced expression and functional characterization of the human ferritin H- and L-chain genes in *Saccharomyces cerevisiae*", Appl. Microbiol Biotechnol (2003) 63: 57-63.
Beard et al., "Purified Ferritin and Soybean Meal Can be Sources of Iron for Treating Iron Deficiency in Rats", Human and Clinical Nutrition, (1995), pp. 154-160.
Roncagliolo et al. "Evidence of Altered Central Nervous System Development in Infants with Iron Deficiency Anemia at 6 mo: Delayed Maturation of Auditory Brainstem Responses", Am. J. Clin. Nutr., 1998, vol. 68, pp. 683-690.
Hulet et al. "Oligodendrocyte Progenitor Cells Internalize Ferritin via Clathrin-Dependent Receptor Mediated Endocytosis", J. Neurosci. Res., Jun. 200, vol. 61, pp. 52-60 (Abstract Only).

* cited by examiner

*Primary Examiner* — Daniel C Gamett
(74) *Attorney, Agent, or Firm* — McCarter & English

(57) ABSTRACT

The present inventors have demonstrated the presence of H-ferritin receptors on endothelial cells in culture and on rat brain rat brain microvasculature, identifying H-ferritin as a means for transporting iron across the blood brain barrier. The present invention provides a method for treating an iron deficiency disorder in a patient, comprising administering to a patient in need thereof a therapeutically effective amount of a ferritin-iron complex. In an embodiment of the invention, the ferritin-iron complex comprises H-ferritin. In another embodiment, the iron deficiency disorder comprises an iron deficiency in the brain. The present invention also provides a method for delivering iron to the brain, comprising administering iron in the form of a ferritin-iron complex to a patient, whereby said iron is transported across the blood-brain barrier and delivered to the brain; a method for using H-ferritin as a targeting moiety, comprising attaching H-ferritin to a liposome, whereby said liposome is targeted to the brain and/or cells within the brain; and a method for treating an iron overload disorder in a patient, comprising administering to a patient in need thereof a therapeutically effective amount of a multi subunit ferritin complex, wherein said multi subunit ferritin complex is at less than 100% iron binding capacity.

5 Claims, 20 Drawing Sheets

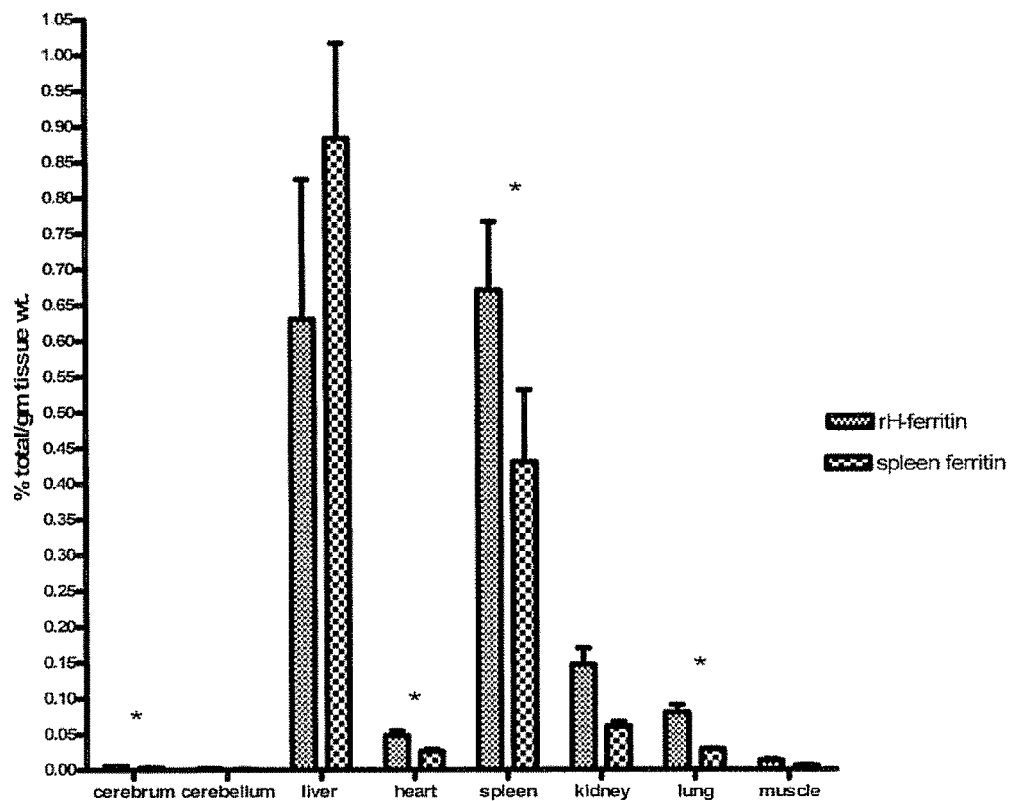
Figure 1a. In vivo uptake of $^{59}$Fe from H-ferritin and spleen ferritin in organs after 48hrs circulation.

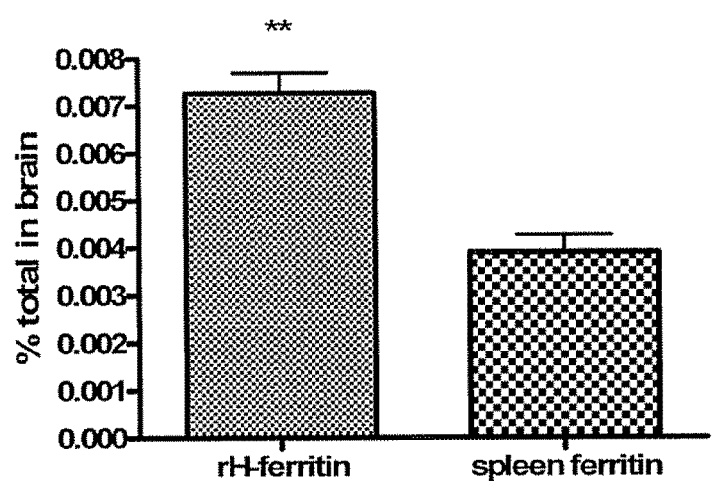
Figure 1b. In vivo uptake of $^{59}$Fe from H-ferritin and spleen ferritin in rat brain.

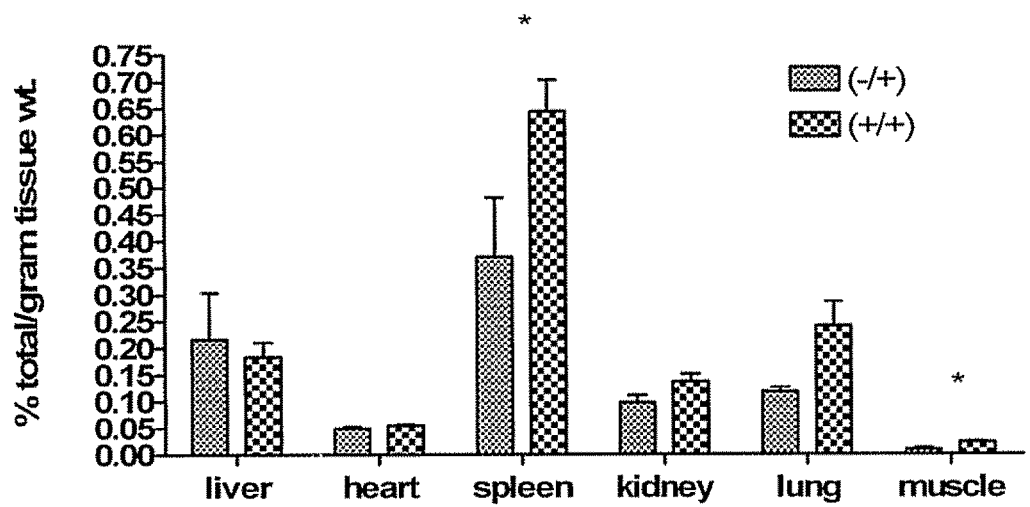
Figure 2A. $^{59}$Fe uptake from H-ferritin into systemic organs in H-ferritin deficient mice (-/+) and wild type (+/+) mice.

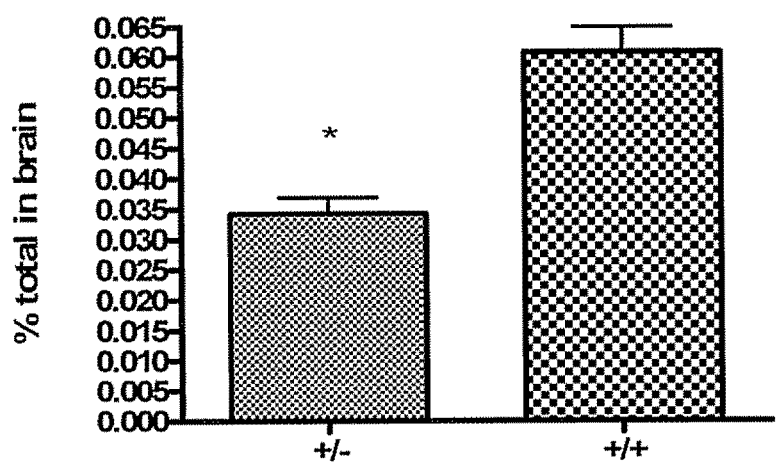
Figure 2b. $^{59}$Fe uptake in brains of H-ferritin deficient mice (+/-) vs. wild type (+/+) mice brains delivered via H-ferritin.

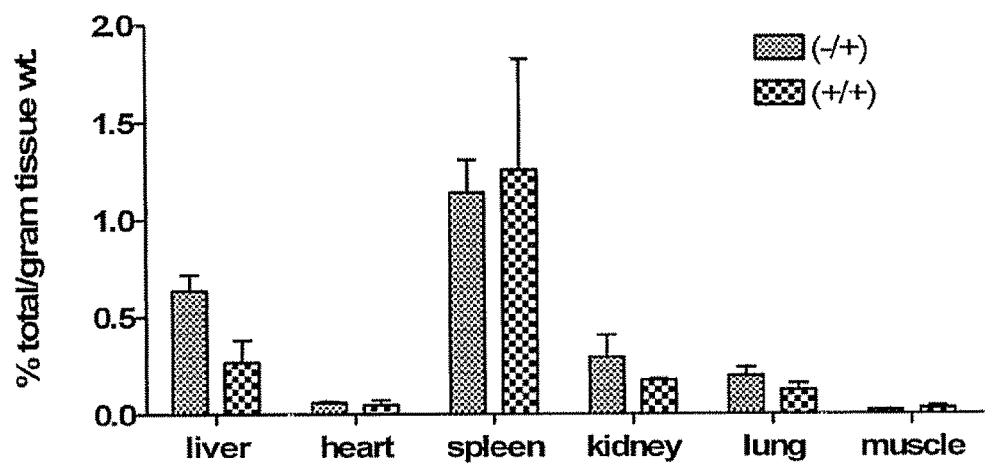
Figure 3a. $^{59}$Fe uptake in various systemic organs in H-ferritin deficient (-/+) and wild type (+/+) mice delivered via spleen ferritin.

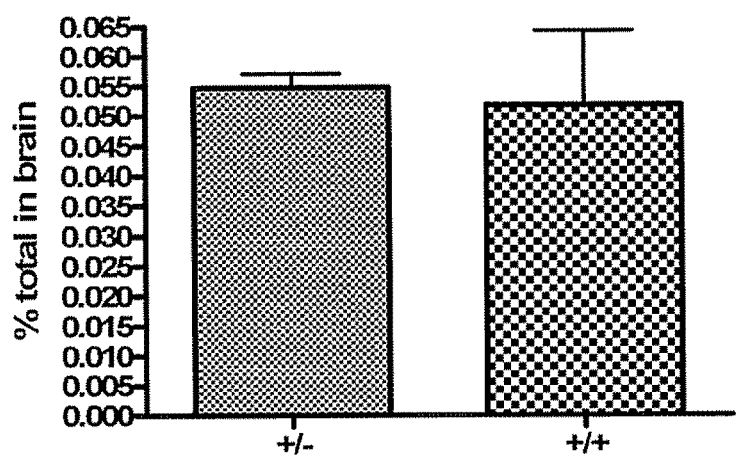
Figure 3b. $^{59}$Fe uptake in the brain in H-ferritin deficient (+/-) vs. wild type (+/+) mice brains delivered via spleen ferritin.

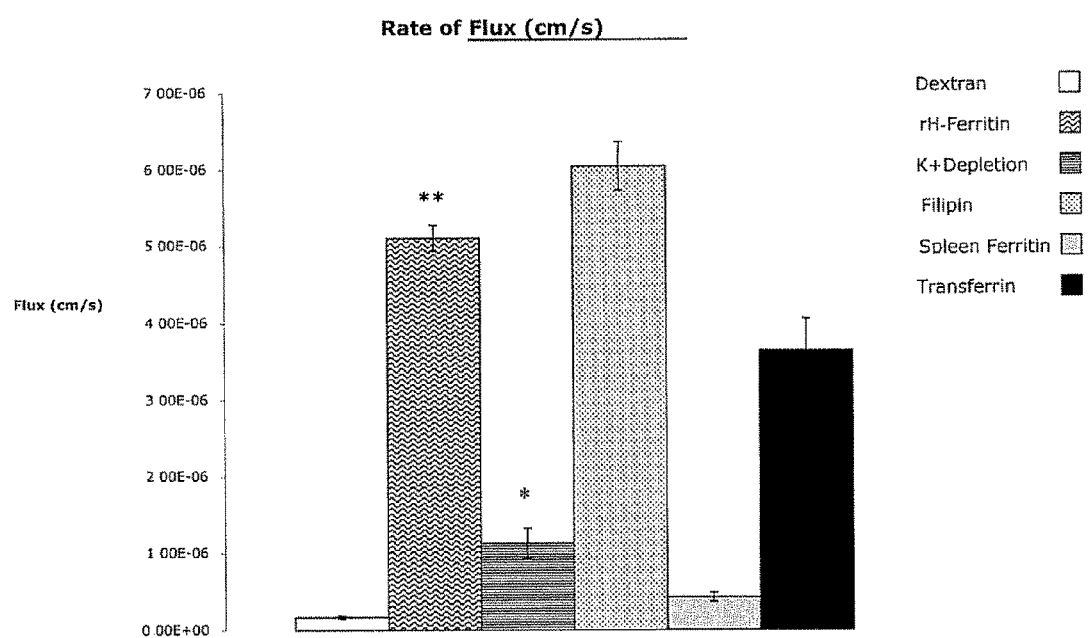
Figure 4a. Flux of Flourescein labeled H-ferritin and spleen ferritin across a BREC culture monolayer.

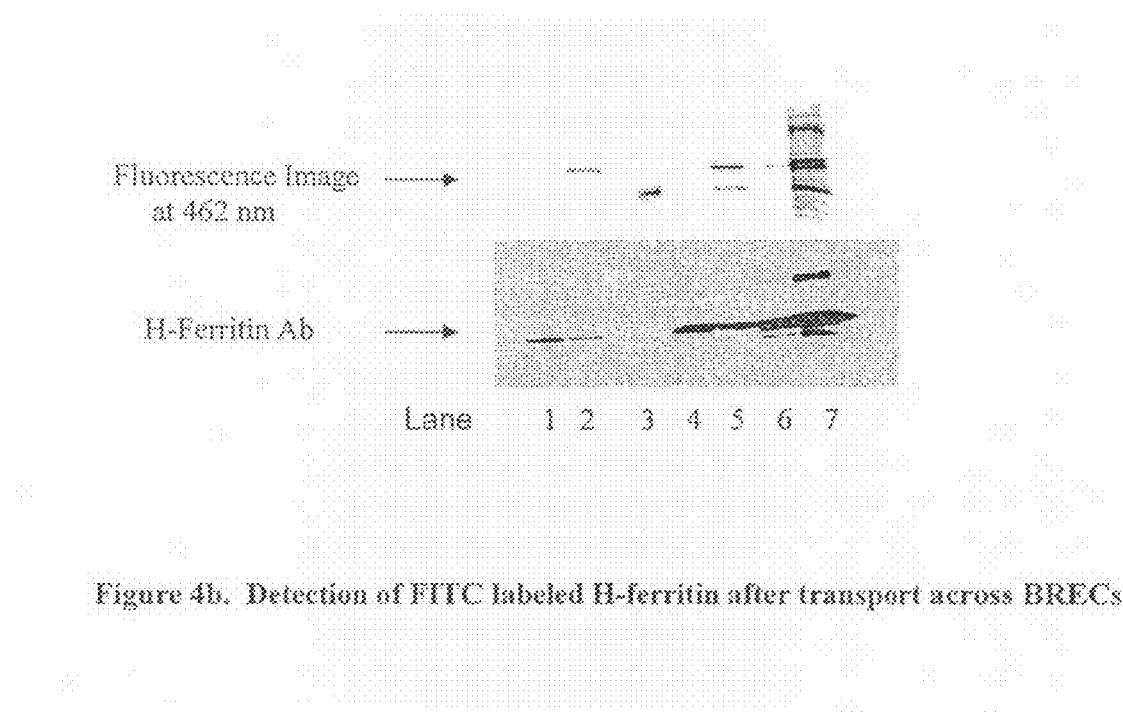
Figure 4b. Detection of FITC labeled H-ferritin after transport across BRECs.

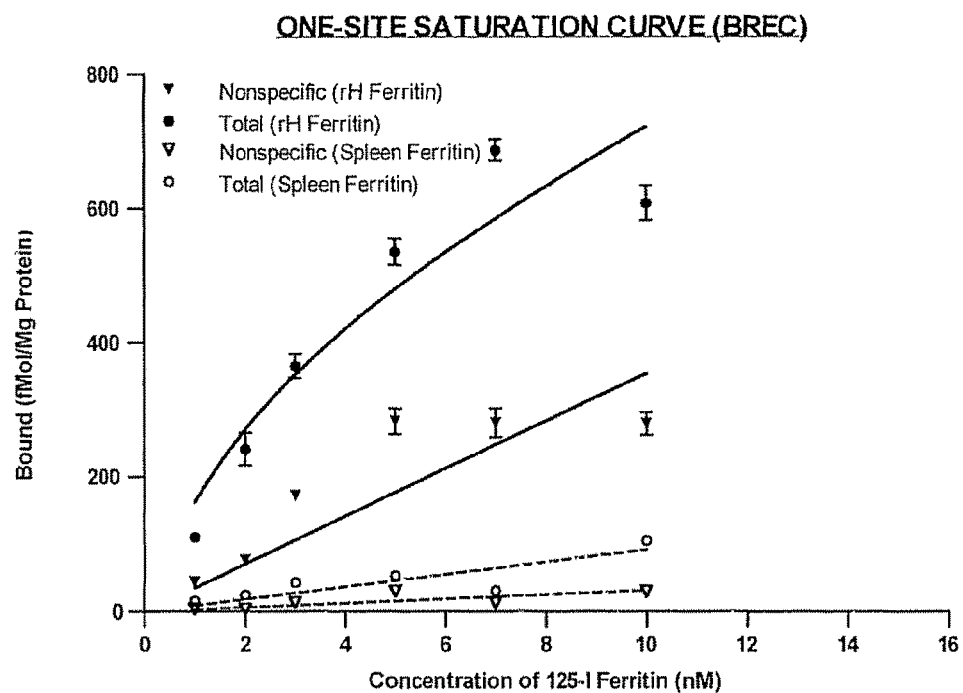
Figure 5a. Saturation curves for $^{125}$I-H-ferritin and $^{125}$I-spleen-ferritin binding to BREC cell homogenates.

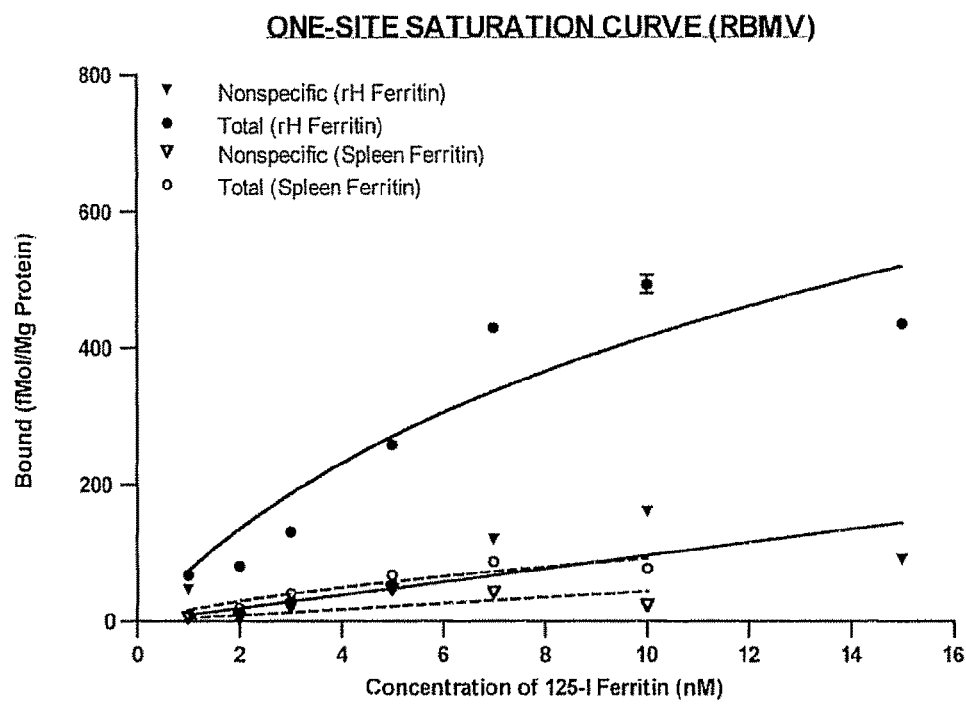
Figure 5b. Saturation curves for $^{125}$I–H-ferritin and $^{125}$I-spleen-ferritin on microvessels isolated from rat brains.

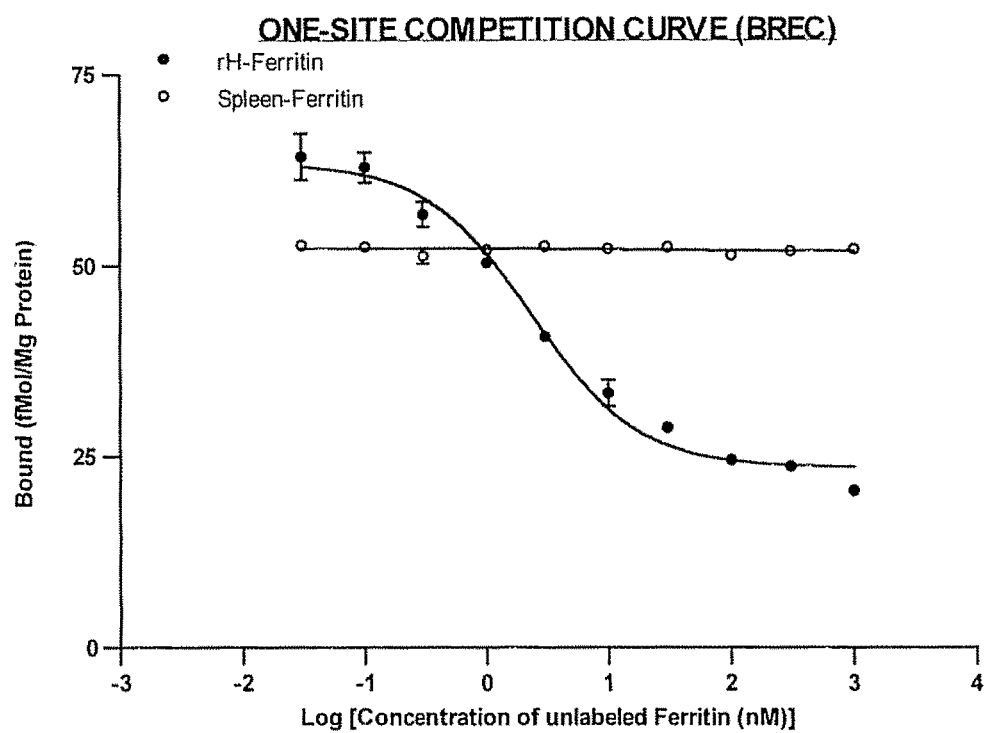
Figure 6a. Competition for $^{125}$I-H-ferritin binding sites on the BREC homogenate by unlabelled H-ferritin and spleen ferritin.

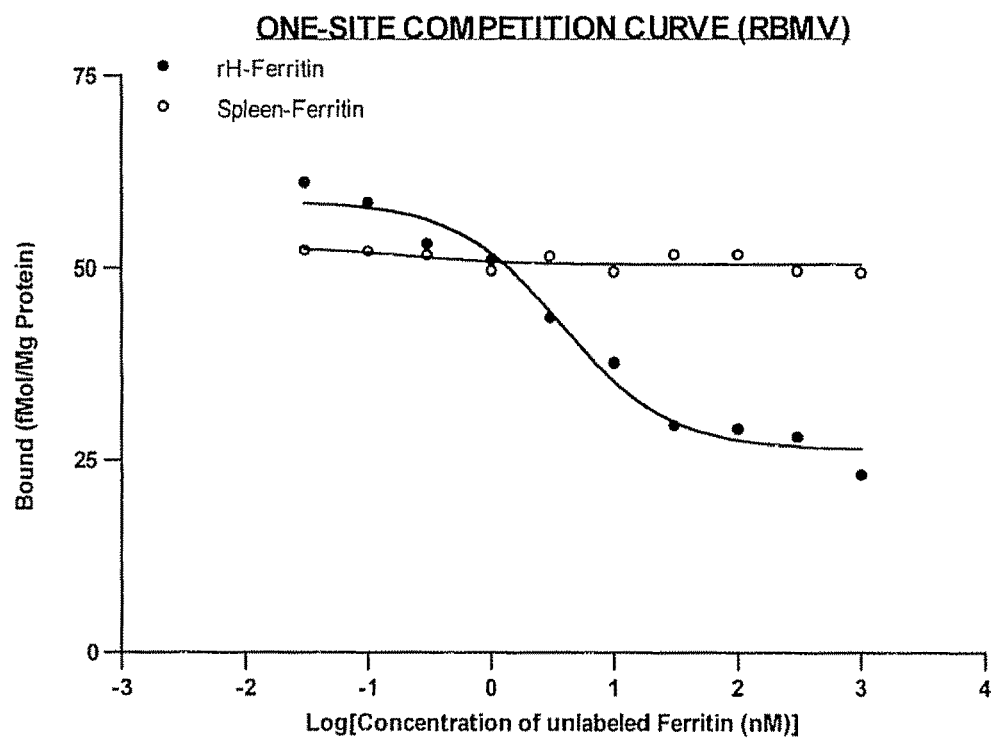
Figure 6b. Competition binding assay on rat microvessels.

Figure 14a

MTTASTSQVRQNYHQDSEAAINRQINLELYASYVYLSMSYYFDRDDVALKNFAKYFL
HQSHEEREHAEKLMKLQNQRGGRIFLQDIKKPDCDDWESGLNAMECALHLEKNVNQS
LLELHKLATDKNDPHLCDFIETHYLNEQVKAIKELGDHVTNLRKMGAPESGLAEYLF
DKHTLGDSDNES

Figure 14b

ATGGCTGATATC
GGATCCATACATATGACGACCGCGTCCACCTCGCAGGTGCGCCAGAACTACCACCAG
GACTCAGAGGCCGCCATCAACCGCCAGATCAACCTGGAGCTCTACGCCTCCTACGTT
TACCTGTCCATGTCTTACTACTTTGACCGCGATGATGTGGCTTTGAAGAACTTTGCC
AAATACTTTCTTCACCAATCTCATGAGGAGAGGGAACATGCTGAGAAACTGATGAAG
CTGCAGAACCAACGAGGTGGCCGAATCTTCCTTCAGGATATCAAGAAACCAGACTGT
GATGACTGGGAGAGCGGGCTGAATGCAATGGAGTGTGCATTACATTTGGAAAAAAAT
GTGAATCAGTCACTACTGGAACTGCACAAACTGGCCACTGACAAAAATGACCCCCAT
TTGTGTGACTTCATTGAGACACATTACCTGAATGAGCAGGTGAAAGCCATCAAAGAA
TTGGGTGACCACGTGACCAACTTGCGCAAGATGGGAGCGCCCGAATCTGGCTTGGCG
GAATATCTCTTTGACAAGCACACCCTGGGAGACAGTGATAATGAAAGCTAACCTAGG
CACCTCGAG

SEQUENCE LISTING

<160> NUMBER OF SEQ ID NOS: 2

<210> SEQ ID NO 1
<211> LENGTH: 183
<212> TYPE: PRT
<213> ORGANISM: Homo sapiens

<400> SEQUENCE: 1

Met Thr Thr Ala Ser Thr Ser Gln Val Arg Gln Asn Tyr His Gln Asp
1               5                   10                  15

Ser Glu Ala Ala Ile Asn Arg Gln Ile Asn Leu Glu Leu Tyr Ala Ser
            20                  25                  30

Tyr Val Tyr Leu Ser Met Ser Tyr Tyr Phe Asp Arg Asp Asp Val Ala
        35                  40                  45

Leu Lys Asn Phe Ala Lys Tyr Phe Leu His Gln Ser His Glu Glu Arg
    50                  55                  60

Glu His Ala Glu Lys Leu Met Lys Leu Gln Asn Gln Arg Gly Gly Arg
65                  70                  75                  80

Ile Phe Leu Gln Asp Ile Lys Lys Pro Asp Cys Asp Asp Trp Glu Ser
                85                  90                  95

Gly Leu Asn Ala Met Glu Cys Ala Leu His Leu Glu Lys Asn Val Asn
            100                 105                 110

Gln Ser Leu Leu Glu Leu His Lys Leu Ala Thr Asp Lys Asn Asp Pro
        115                 120                 125

His Leu Cys Asp Phe Ile Glu Thr His Tyr Leu Asn Glu Gln Val Lys
    130                 135                 140

Ala Ile Lys Glu Leu Gly Asp His Val Thr Asn Leu Arg Lys Met Gly
145                 150                 155                 160

Ala Pro Glu Ser Gly Leu Ala Glu Tyr Leu Phe Asp Lys His Thr Leu
                165                 170                 175

Gly Asp Ser Asp Asn Glu Ser
            180

<210> SEQ ID NO 2
<211> LENGTH: 591
<212> TYPE: DNA
<213> ORGANISM: Homo sapiens

<400> SEQUENCE: 2
atggctgata tcggatccat acatatgacg accgcgtcca cctcgcaggt gcgccagaac      60
taccaccagg actcagaggc cgccatcaac cgccagatca acctggagct ctacgcctcc     120
tacgtttacc tgtccatgtc ttactacttt gaccgcgatg atgtggcttt gaagaacttt     180
gccaaatact tcttcacca atctcatgag gagagggaac atgctgagaa actgatgaag      240
ctgcagaacc aacgaggtgg ccgaatcttc cttcaggata tcaagaaacc agactgtgat     300
gactgggaga gcgggctgaa tgcaatggag tgtgcattac atttggaaaa aaatgtgaat     360
cagtcactac tggaactgca caaactggcc actgacaaaa atgaccccca tttgtgtgac     420
ttcattgaga cacattacct gaatgagcag gtgaaagcca tcaaagaatt gggtgaccac     480
gtgaccaact tgcgcaagat gggagcgccc gaatctggct tggcggaata tctctttgac     540
aagcacaccc tgggagacag tgataatgaa agctaaccta ggcacctcga g              591

USE OF FERRITIN TO TREAT IRON DEFICIENCY DISORDERS

CONTINUING APPLICATION DATA

This application claims benefit of U.S. Provisional Application Nos. 60/886,972 and 60/984,007, filed Jan. 29, 2007 and Oct. 31, 2007, respectively, both of which are incorporated by reference herein in their entirety.

BACKGROUND OF THE INVENTION

Ferritin, the main intracellular iron storage protein in both prokaryotes and eukaryotes, is a large (nearly 480 kDa) multi-subunit complex comprising 24 polypeptide subunits. This iron storage complex, found in high concentrations in serum, is capable of containing as many as 4,500 atoms of iron ions ($Fe^{3+}$) within a hydrous ferric oxide core. In mammals, there are two distinct subunit classes, heavy (H) and light (L) type with a molecular weight of about 21 kDa and 19 kDa, respectively, which share about 54% sequence identity. The H and L subunits appear to have different functions: the L subunit enhances the stability of the iron core while the H subunit has a ferroxidase activity that appears to be necessary for the rapid uptake of ferrous iron. H rich ferritins are localized in tissues undergoing rapid changes in local ion concentration. For instance, expression of the H subunit is preferentially increased relative to the L subunit in cells undergoing differentiation, development, proliferation and metabolic stress.

The brain imposes heightened challenges to iron acquisition because of the highly developed tight junctions that bind neighboring endothelial cells that make up the brain microvasculature. These junctions prevent the paracellular flux of molecules into the brain. The resulting blood-brain barrier (BBB) is a highly effective mechanism for protecting the brain from potentially harmful substances that circulate in the blood. A consequence of such a blockade, however, is that specific transport mechanisms must be designed for the many trophic substances that are required for normal brain function. Pinocytosis is a potential method to circumvent the BBB, but vesicles that arise from pinocytosis contribute relatively little to nonspecific transport of compounds across the brain vascular endothelial cells.

Traditionally, transferrin has been considered the primary mechanism for cellular iron delivery, and a transferrin mediated transport system has been identified in the BBB (Jefferies W. A., et al. Nature 312: 162-163, 1984; Fishman J., Rubin J., Handrahan J., Connor J., Fine R. J. Neurosci. Res. 18: 299-304, 1987). However, transferrin-independent iron delivery to the brain has been suggested using hypotransferrinemic mice (Malecki E. A., Cook B. M., Devenyi A. G., Beard J. L. and Connor J. R. J. Neurol. Sci. 170: 112-118, 1999). It has been proposed that lactoferrin may also transport iron into the brain (Ji B., et al. Life Sci. 78: 851-855, 2005), but lactoferrin concentrations in serum are barely detectable and this protein is generally found within cells (neutrophils) and is thus unlikely to contribute to iron transport to the brain or other organs.

SUMMARY OF THE INVENTION

The present inventors have surprisingly found that ferritin, long considered an iron storage protein, can function as an iron delivery protein. In particular, the present inventors have demonstrated the presence of H-ferritin receptors on endothelial cells in culture and on rat brain microvasculature, identifying H-ferritin as a means for transporting iron across the BBB. The present invention provides a method for treating an iron deficiency disorder in a patient, comprising administering to a patient in need thereof a therapeutically effective amount of a ferritin-iron complex. In an embodiment of the invention, the ferritin-iron complex comprises H-ferritin. In another embodiment, the iron deficiency disorder comprises an iron deficiency in the brain. The present invention also provides a method for delivering iron to the brain, comprising administering iron in the form of a ferritin-iron complex to a patient, whereby said iron is transported across the blood-brain barrier and delivered to the brain; a method for using H-ferritin as a targeting moiety, comprising attaching H-ferritin to a liposome, whereby said liposome is targeted to the brain and/or cells within the brain; and a method for treating an iron overload disorder in a patient, comprising administering to a patient in need thereof a therapeutically effective amount of a multi subunit ferritin complex, wherein said multi subunit ferritin complex is at less than 100% iron binding capacity.

BRIEF DESCRIPTION OF THE DRAWINGS

FIG. 1A shows the in vivo uptake of $^{59}Fe$ from recombinant human H ferritin (rH-ferritin) as compared to horse spleen ferritin (spleen ferritin) in organs after 48 hrs circulation. The $^{59}Fe$ labeled H or spleen ferritin was injected into adult rat tail veins and allowed to circulate for 48 hours. The amount of radioactivity was determined in 1.0 gram of each organ and the % total/gm tissue weight was determined by calculating the amount of µC per organ compared to the total injected. The two brain structures are shown on this scale to reveal the relative amounts. The data presented are the mean of 3 animals±S.E. p<0.05*.

FIG. 1B shows the in vivo uptake of $^{59}Fe$ from ferritin in rat brain. Rats were injected via the tail vein with $^{59}Fe$ labeled H or spleen ferritin as described in the legend for FIG. 1A. The % total was calculated by determining the µC in one hemisphere of the brain/total µC injected×100%. p<0.005**. The data presented are a mean of 3 animals±S.E.

FIG. 2A shows the $^{59}Fe$ uptake from H-ferritin into systemic organs in H-ferritin deficient mice (−/+) and wild type (+/+) mice. Animals received equal amounts of H-ferritin injected intraperitoneally. The ferritin circulated for 48 hours. The organs shown (including the brain) were removed and the percent of total radioactivity determined for each organ based on 0.1 g. p<0.05*.

FIG. 2B shows the $^{59}Fe$ uptake in brains of H-ferritin deficient mice (+/−) vs. wild type (+/+) mice brains delivered via H-ferritin. These data are from the brains of the mice that were used to generate the data in FIG. 2A. The % of radioactivity in the brain was determined by comparing the disintegration counts/min of $^{59}Fe$ obtained from the brain to the total µC injected. p<0.05*. The results shown are the mean of three animals±the standard error.

FIG. 3A shows $^{59}Fe$ uptake in various systemic organs in H-ferritin deficient (−/+) and wild type (+/+) mice delivered via spleen ferritin. Mice were injected intraperitoneally with spleen ferritin containing $^{59}Fe$. After 48 hours the mice were killed and the organs removed. The amount of radioactivity was determined in 0.1 g of each organ and the percent of total injected radioactivity determined and presented in this graph. The data are the mean of three animals±S.E. None of the differences reached statistical significance.

FIG. 3B shows $^{59}Fe$ uptake in the brain in H-ferritin deficient (+/−) vs. wild type (+/+) mice brains delivered via spleen ferritin. These data are from the mice used in FIG. 3A. The amount of radioactivity reported is the % of the total injected into the animals. The results shown are the mean of three animals±the standard error.

FIG. 4 is a graph showing flux of fluorescein labeled H ferritin across a BREC culture monolayer. This graph shows the transport rate of FITC labeled H ferritin in the basal chamber over 4 hours. The rate of transport was determined as described in the Methods section. The data shown are the means of the rate of flux, obtained as the slope (cm/s) from the plots of bottom chamber fluorescence per unit amount of top chamber fluorescence (Bf/Tf) versus time and the standard error of the means. H-ferritin transport is statistically significant compared to the dextran control and spleen ferritin (p<0.01)**. Spleen-ferritin transport was no different from the dextran control. Pretreatment of the BRECs with potassium depleted media resulted in a significant decrease in FITC H-ferritin transport (p<0.05)* but pretreatment with filipin to minimize pinocytosis had no effect on the rate of H-ferritin transport. Transferrin transport was included as a positive control. The values shown for dextran flux are for the untreated control samples, but the rate of dextran flux did not change with any of the treatments (data not shown).

FIG. 5A is a graph showing the saturation curves for $^{125}$I-H-ferritin and $^{125}$I-spleen-ferritin binding to BREC cell homogenates. This graph illustrates that H-ferritin binding to BREC cells is saturable whereas there is no evidence of binding of spleen ferritin. Saturation binding was performed at 4° C. for 2 hours. The $K_d$ was determined to be is 2.7±0.9 nM and the $B_{max}$ is 465.7±63.1 fmol/mg protein.

FIG. 5B shows saturation curves for $^{125}$I-H-ferritin and $^{125}$I-spleen-ferritin on microvessels isolated from rat brains. The curves show saturable binding for H-ferritin but no binding for spleen ferritin. The $K_d$ is 7.9±1.6 nM and $B_{max}$ is 572.6±64.0 fmol/mg protein.

FIG. 6A is a graph showing competition for $^{125}$I-H-ferritin binding sites on the BREC homogenate by unlabelled H-ferritin and spleen ferritin. This graph shows that the binding of $^{125}$I-H-ferritin to the BREC homogenate is competitively inhibited by increasing concentrations of unlabelled H-ferritin, but not with spleen ferritin.

FIG. 6B is a graph showing competition binding assay on rat microvessels. This graph illustrates that binding of $^{125}$I H-ferritin can be dissociated in a concentration dependent manner by unlabeled H-ferritin but not by unlabeled spleen ferritin.

FIG. 14A shows the amino acid sequence of human H-ferritin (SEQ ID NO: 1).

FIG. 14B shows the cDNA sequence of human H-ferritin (SEQ ID NO: 2). The start (ATG) and stop (TAA) codons are bolded, and the BamHI (at 5' end of sequence) and XhoI (at 3' end of sequence) restrictions sites are underlined.

DETAILED DESCRIPTION OF THE INVENTION

Figure 7:
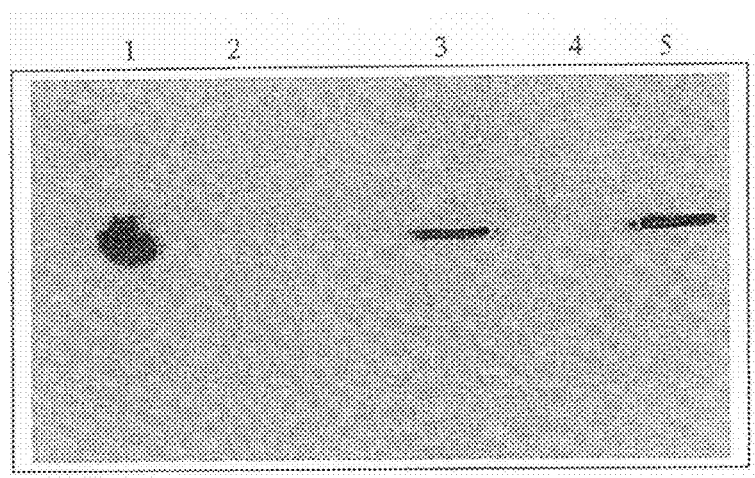
FIG. 7 is a Western blot (4-20% gradient) showing expression of H-ferritin in recombinant yeast. In Lane 1 is a standard (recombinant human H-ferritin). Lanes 2 and 4 are two different colonies of yeast that were transformed with human L-ferritin. Lanes 3 and 5 are two different yeast colonies that were transformed with human H-ferritin. The antibody used in this study is anti-HF HS-59 (1:40,000 for 16 hours) which is a mouse monoclonal to H-ferritin generously supplied by Paolo Arosio (Brescia Italy).

The present invention provides a method for treating an iron deficiency disorder in a patient, comprising administering to a patient in need thereof a therapeutically effective amount of a ferritin-iron complex.

As used herein, an "iron deficiency disorder" includes a disorder or disease related to iron deficiency, iron uptake, and/or iron metabolism. Examples of iron deficiency disorders include iron deficiency anemia, such as iron deficiency anemia caused by insufficient dietary intake or absorption of iron. Iron deficiency anemia may be related to, for example, malnutrition, pregnancy (including the postpartum period), heavy uterine bleeding, chronic disease (including chronic kidney disease), cancer, renal dialysis, gastric by-pass, multiple sclerosis, diabetes (e.g. Type I and Type II diabetes), insulin resistance, and attention deficit disorders.

In one embodiment of the invention, the iron deficiency disorder is related to deficient iron levels in the brain, such as occurs in various neurological and neurodegenerative diseases including Parkinson's disease, Alzheimer's disease, Restless Legs Syndrome (RLS), suboptimal cognitive performance associated with anemia in women, depression and insomnia. In another embodiment, the iron deficiency disorder comprises neurological deficit(s) associated with brain iron deficiency during postnatal development, including hypomyelination and slow brain development resulting from developmental iron deficiency leading to poor cognitive performance and motor impairments.

Lack of iron and reduced dopamine synthesis in the brain are important factors in iron deficiency disorders such as, for example, RLS and developmental iron deficiency in children. Dopamine is a neural transmitter synthesized in the brain that is essential for proper central nervous system (CNS) function. In the synthesis of dopamine, iron is a cofactor for the enzyme tyrosine hydroxylase, which is the rate-limiting step in dopamine metabolism (Cooper et al. (1991) The biochemical basis of neuropharmacology. Oxford University Press, New York, N.Y.). Iron in the dopaminergic system appears to be an important component in RLS pathophysiology and in behavioral deficits in children, including Attention Deficit Hyperactivity Disorder (ADHD). RLS patients have 65% less cerebral spinal fluid (CSF) ferritin and three-fold more CSF transferrin (iron transport blood protein), despite normal serum levels of ferritin and transferrin in both RLS and controls. Iron concentrations vary throughout the brain, the site of dopamine synthesis; RLS patients have less iron in the substantia nigra and in the putamen parts of the brain. In general, decreased ferritin levels are indicative of RLS severity. Reports also exist of decreased serum ferritin levels in children with ADHD.

The term "ferritin-iron complex" refers to a protein complex comprising multiple ferritin subunits and iron atoms. Suitable ferritin-iron complexes comprise mammalian H-ferritin subunits. The amino acid sequences of H-ferritin subunits from various mammalian species have been identified. See, e.g., Orino Koichi et al., *Sequence analysis of feline ferritin H and L subunit cDNAs*; Veterinary Biochem. 42:7-11 (2005); Accession number: 06A006486. In one embodiment, the H-ferritin is human H-ferritin (SEQ ID NO: 1; see FIG. 14A). The H-ferritin can also be a naturally-occurring or synthetic homologue or variant of human H-ferritin. In certain embodiments, the H-ferritin homologue has about 80% to about 100% sequence identity to human H-ferritin, such as at least 80%, 81%, 82%, 83%, 84%, 85%, 86%, 87%, 88%, 89%, 90%, 91%, 92%, 93%, 94%, 95%, 96%, 97%, 98%, or 99% sequence identity with human H-ferritin. The H-ferritin homologue retains the ability to bind iron and form a multi-subunit ferritin-iron complex, but can be mutated to provide varying binding and disassociation strengths between the iron and the ferritin. The ferritin-iron complex comprises H-ferritin subunits, but can also comprise some L-ferritin subunits. In certain embodiments, the ferritin subunit component of the complex comprises at least 20% H-ferritin as compared to L-ferritin, such as about 20%, 30%, 40%, 50%, 60%, 70%, 80%, 90%, or 100% H-ferritin as compared to L-ferritin. In one embodiment, all of the ferritin subunits in the ferritin-iron complex (i.e. 100% of the ferritin subunits) are H-ferritin. The H-ferritin can be recombinant H-ferritin. For example, the H-ferritin can be human H-ferritin, or a homologue thereof, produced in a yeast strain comprising a polynucleotide sequence encoding the H-ferritin under the control of an appropriate yeast promoter.

The iron in the ferritin-iron complex can be an iron molecule, or can be in the form of an iron containing complex. "Iron containing complexes" or "iron complexes" are compounds which contain iron in the (II) or (III) oxidation state, complexed with an organic compound. Iron complexes include iron polymer complexes, iron carbohydrate complexes, and iron aminoglycosan complexes. These complexes are commercially available and/or can be synthesized by methods known in the art.

Examples of iron carbohydrate complexes include iron saccharide complexes, iron oligosaccharide complexes, and iron polysaccharide complexes, such as iron carboxymaltose, iron sucrose, iron polyisomaltose (iron dextran), iron polymaltose (iron dextrin), iron gluconate, iron sorbital, and iron hydrogenated dextran, which may be further complexed with other compounds, such as sorbitol, citric acid and gluconic acid (for example iron dextrin-sorbitol-citric acid complex and iron sucrose-gluconic acid complex), and mixtures thereof.

Examples of iron aminoglycosan complexes include iron chondroitin sulfate, iron dermatin sulfate, iron keratan sulfate, which may be further complexed with other compounds and mixtures thereof. Examples of iron polymer complexes include iron hyaluronic acid, iron protein complexes, and mixtures thereof.

"Treatment" or "treating," as used herein, refers to complete elimination as well as to any clinically or quantitatively measurable reduction in the condition for which the patient or subject is being treated. "Treatment" is an intervention performed with the intention of preventing the development or altering the pathology or symptoms of a disorder. Accordingly, "treatment" refers to both therapeutic treatment and prophylactic or preventative measures. "Treatment" may also be specified as palliative care. Those in need of treatment include those already with one or more iron-deficiency disorder as well as those in which the disorder is to be prevented.

In treating a patient in need thereof, a therapeutically effective amount of the present ferritin-iron composition is administered thereto in accordance with the present invention. As used herein, the term "therapeutically effective amount" is an amount of the composition indicated for treatment while not exceeding an amount which may cause significant adverse effects. Methods for evaluating the effectiveness of therapeutic treatments are known to those of skill in the art.

A "patient in need thereof" refers to any patient or subject who could benefit from the inventive method of treatment. In certain embodiments, a patient in need thereof is a patient predisposed for the development of one or more iron deficiency disorders, a subject having one or more iron deficiency disorders but not exhibiting any clinical symptoms, or a subject having one or more iron deficiency disorders and suffering from the symptoms of the one or more iron deficiency disorders. The patient in need thereof may be a mammal, such as a human, a dog, a cat, a cow, a horse, a rodent (such as a mouse, a rat, or a hamster), or a primate. In one embodiment, the patient is a human. In certain embodiments, the inventive methods find use in experimental animals, in veterinary application, and/or in the development of animal models for disease.

Doses to be administered are variable according to the treatment period, frequency of administration, the host, and the nature and severity of the disorder. The dose can be determined by one of skill in the art without an undue amount of experimentation. The compositions of the invention are administered in dosage concentrations sufficient to ensure the release of a sufficient dosage unit of the ferritin-iron complex into the patient to provide the desired treatment of the iron deficiency disorder. The actual dosage administered will be determined by physical and physiological factors such as age, body weight, severity of condition, and/or clinical history of the patient. The active ingredients may be administered to achieve in vivo plasma concentrations of the ferritin-iron complex of from about 50 µM to about 1000 µM. For example, the methods of the present invention may use compositions to provide from about 0.1 to about 1,000 or from about 1 to about 100 mg/kg body weight/day of the ferritin-iron complex, such as about 30 mg/kg body weight/day of the ferritin-iron complex. It will be understood, however, that dosage levels that deviate from the ranges provided may also be suitable in the treatment of a given disorder.

The ferritin-iron complexes of the present invention may be in any form suitable for administration. Such administrable forms include tablets, buffered tablets, pills, capsules, enteric-coated capsules, dragees, cachets, powders, granules, aerosols, liposomes, suppositories, creams, lotions, ointments, skin patches, parenterals, lozenges, oral liquids such as suspensions, solutions and emulsions (oil-in-water or water-in-oil), ophthalmic liquids and injectable liquids, or sustained-release forms thereof. The desired dose may be provided in several increments at regular intervals throughout the day, by continuous infusion, or by sustained release formulations, or may be presented as a bolus, electuary or paste.

In one embodiment, a pharmaceutical composition or formulation comprising the ferritin-iron complexes is prepared by admixture with one or more pharmaceutically acceptable carriers. In some cases, the ferritin-iron complex may be delivered as a composition comprising ferritin-iron complexes and the buffer in which the iron molecules and the ferritin molecules were dissolved in order to allow for iron-ferritin binding (i.e. formation of the ferritin-iron complexes). However, other products may be added, if desired, to maximize iron delivery, preservation, or to optimize a particular method of delivery. In addition, the present invention includes use of combination compositions comprising the ferritin-iron complexes as described herein in combination with other agents suitable for the treatment of iron deficiency disorders.

As used herein, "pharmaceutically acceptable" means acceptable for use in the pharmaceutical and veterinary arts, compatible with other ingredients of the formulation, and not toxic or otherwise unacceptable commensurate with a reasonable benefit/risk ratio. A "pharmaceutically acceptable carrier" or "diluent" includes any and all solvents, dispersion media, coatings, antibacterial and anti-fungal agents, isotonic and absorption delaying agents, and the like, compatible with pharmaceutical administration of a composition comprising ferritin-iron complexes. Examples of such carriers or diluents include, but are not limited to, water, saline, Finger's solutions and dextrose solution. The volume of the pharmaceutical composition is based on the intended mode of administration and the safe volume for the individual patient, as determined by a medical professional.

The selection of carrier also depends on the intended mode of administration. Compositions of the present invention may be administered by any of a number of convenient means including, but not limited to systemic administration (e.g. intravenous injection, intraparenteral injection, inhalation, transdermal delivery, oral delivery, nasal delivery, rectal delivery, etc.) and/or local administration (e.g. direct injection into a target tissue, delivery into a tissue via cannula, delivery into a target tissue by implantation of a time-release material), delivery into a tissue by a pump, etc., orally, parenterally, intraosseously, in the cerebrospinal fluid, or the like. Further modes of administration include buccal, sublingual, vaginal, subcutaneous, intramuscular, or intradermal administration.

In one embodiment, compositions to be administered orally are prepared using substances that are suitably combined with ferritin-iron complexes for oral ingestion. Such substances include, without limitation, sugars, such as lactose (hydrous, fast flow), glucose and sucrose; starches such as corn starch and potato starch; cellulose and derivatives thereof, including microcrystalline cellulose, sodium carboxymethylcellulose, ethylcellulose and cellulose acetates; powdered tragacanth; colloidal silicon dioxide; croscarmellose sodium; malt; gelatin; talc; stearic acids; magnesium stearate; calcium sulfate; vegetable oils, such as peanut oils, cotton seed oil, sesame oil, olive oil and corn oil; polyols such as propylene glycol, glycerine, sorbitol, mannitol and polyethylene glycol; agar; alginic acids; antacids such as aluminum hydroxide or magnesium hydroxide; buffer such as sodium citrate, acetate, or bicarbonate; water; isotonic saline and phosphate buffer solutions. Wetting agents, lubricants such as sodium lauryl sulfate, stabilizers, tabletting agents, anti-oxidants, preservatives, coloring agents and flavoring agents may also be present.

Compositions or formulations suitable for parenteral administration include aqueous and non-aqueous, isotonic sterile injection solutions which may contain antioxidants, buffers, bacteriostats or solutes which render the formulation isotonic with blood; and aqueous and non-aqueous sterile suspensions which may include suspending agents and thickening agents. The compositions may be presented in unit-dose or multi-dose sealed containers, for example, ampoules and vials, and may be stored in a freeze-dried (lyophilized) condition requiring only the addition of the sterile liquid carrier, for example, water for injections, immediately prior to use. Extemporaneous injection solutions and suspensions may be prepared from sterile powders, granules or tablets, or the like.

Compositions or formulations suitable for intravenous administration comprise carriers such as physiological saline, bacteriostatic water, CREMOPHOR EL™ (BASF; Parsippany, N.J.) or phosphate buffered saline (PBS). The composition must be sterile and should be fluid so as to be administered using a syringe. Such compositions should be stable during manufacture and storage and must be preserved against contamination from microorganisms, such as bacteria and fungi. The carrier can be a dispersion medium containing, for example, water, polyolo (such as glycerol, propylene glycol, and liquid polyethylene glycol), and other compatible, suitable mixtures. Various antibacterial and anti-fungal agents, for example, parabens, chlorobutanol, phenol, ascorbic acid, and thimerosal, can contain microorganism contamination. Isotonic agents such as sugars, polyalcohols, such as mannitol, sorbitol, and sodium chloride can be included in the composition. Compositions that can delay absorption include agents such as aluminum monostearate and gelatin. Methods of preparation of sterile solids for the preparation of sterile injectable solutions include vacuum drying and freeze-drying to yield a solid containing the ferritin-iron complex and any other desired ingredient.

Systemic administration can be, for example, transmucosal or transdermal. For transmucosal or transdermal administration, penetrants that can permeate the target barrier(s) are selected. Transmucosal penetrants include, detergents, bile salts, and fusidic acid derivatives. Nasal sprays or suppositories can be used for transmucosal administration. For transdermal administration, the active compounds are formulated into ointments, salves, gels, or creams.

Compositions comprising ferritin-iron complexes may be prepared with carriers that protect the complexes against rapid elimination from the body, such as a controlled release formulation, including implants and microencapsulated delivery systems. Biodegradable or biocompatible polymers can be used, such as ethylene vinyl acetate, polyanhydrides, polyglycolic acid, collagen, polyorthoesters, and polylactic acid. Such materials can be obtained commercially from ALZA Corporation (Mountain View, Calif.) and NOVA Pharmaceuticals, Inc. (Lake Elsinore, Calif.), or prepared by one of skill in the art.

Compositions for ophthalmic administration are prepared in suitable liquid carriers such as buffered or physiological saline, liposomes or basic amino acids. Creams, lotions and ointments may be prepared for topical application using an appropriate base such as triglyceride base, liposomes, or basic amino acids. Such creams, lotions and ointments may also contain a surface active agent.

In an embodiment of the present invention, the ferritin-iron complexes are administered in the form of a strain of recombinant yeast expressing H-ferritin. Recombinant yeast strains suitable for nutritional supplementation of iron can store iron in a form having high bioavailability for mammals, including humans. The strain of yeast includes those that meet the Generally Regarded As Safe (GRAS) requirements for human consumption. In this embodiment, the iron-storage gene (e.g. the H-ferritin coding sequence) can be placed under the control of an appropriate yeast promoter in an iron-storage expression cassette to produce levels of the iron-storage protein necessary for the yeast to serve as a suitable vehicle for iron supplementation. Suitable promoters are known in the art, and include promoters that induce a high level of constitutive expression and promoters whose expression can be regulated by environmental conditions. In addition, the genetic constitution of the yeast can be further manipulated to achieve a variety of potentially advantageous outcomes. For example, proteolysis may be manipulated to enhance the stability of the iron-storage protein or iron transport mechanisms, including but not limited to those of the cell surface, the vacuole, or the mitochondria. In addition, the yeast may be altered to enhance the level of iron in the iron-storage protein or cellular compartments. The iron content of the yeast may be regulated by adding known amounts of an iron compound to the medium in which the yeast are grown. Using the recombinant yeast, iron supplementation for humans or other animals can be accomplished by any of a number of means including, but not limited to, consumption of the recombinant yeast as a nutritional supplement or consumption of ferritin-iron complexes purified or isolated from the recombinant yeast. The yeast may be grown specifically for the purpose of iron supplementation or they may be the by-product of another process (e.g. fermentation).

Alternatively, or in addition, ferritin-iron complexes can comprise H-ferritin produced in other expression systems known in the art, including *E. coli*, baculovirus and transgenic animals. In one embodiment, the ferritin-iron complexes can be formed by incubating ferritin subunits and iron molecules in a suitable buffer, followed by separating any unbound iron molecules from the resulting ferritin-iron complexes.

In certain embodiments, the ferrin-iron complex further comprises a targeting moiety, such as an antibody, aptamer, receptor, ligand, or binding fragment thereof. The targeting moiety can recognize one or more cell, tissue and/or organ specific marker, thus mediating or improving delivery to a desired target or location in the body. In one embodiment, the ferritin-iron complex can comprise a fusion protein comprising a ferritin subunit, such as H-ferritin, fused with a targeting peptide. In another embodiment, the ferritin-iron complex may be delivered or administered encapsulated into a liposome, a liposomal construct, or other membrane-bound vesicle such as a red cell ghost. The liposome, liposomal construct or other vesicle can comprise a targeting moiety, such as an antibody or ligand specific for a particular cell surface protein or receptor (see above), incorporated into the liposome or vesicle. The targeting moiety can target the ferritin-iron complex, or the vesicle comprising the ferritin-iron complex, to the brain and/or to the blood brain barrier. Examples of suitable targeting moieties include transferrin, interleukin-13 (for delivery to astrocytomas), and lipopolysaccharide (LPS).

In another embodiment of the invention, H-ferritin itself can be used to target other moieties. For example, H-ferritin can be attached to a biologically active agent in order to deliver that agent to the brain. In one embodiment, the H-ferritin peptide is fused to another biologically active peptide. Alternatively, or in addition, H-ferritin can be conjugated to liposomes or other vesicles to deliver the vesicles and the vesicle contents to the brain. In yet another embodiment, H-ferrtin can be bound to agents such as contrast enhancing compounds to enhance visualization of the brain (e.g. white matter tracts and defects therein). Similar to the biologically active agents, the contrast enhancing compounds can be bound to or within the H-ferritin protein or encapsulated within liposomes or other vesicles that are targeted to H-ferritin receptors in the brain via liposome-conjugated H-ferritin acting as the receptor ligand.

In another embodiment of the invention, H-ferritin can be used to treat disorders related to excess iron or iron overload. Iron overload, clinically known as hemochromatosis, is associated with, for example, increased risk of cancer, heart failure, liver dysfunction and diabetes. Iron overload in the brain can occur in a wide range of neurodegenerative diseases, such as Parkinson's disease, Alzheimer's disease, amyotrophic lateral sclerosis, Hallovordeen-Spatz, and Huntington's disease. Because of the significant iron binding capacity of H-ferritin, H-ferritin and/or multi-subunit complexes comprising H-ferritin can be used as an iron chelator. By "multi-subunit ferritin complex" is meant a protein complex comprising multiple ferritin subunits and optionally iron. The H-ferritin is mammalian ferritin or a homologue or variant thereof as defined above. The multi-subunit ferritin complexes can be prepared in a relatively iron-free environment so that the resulting complex is at less than 100% of its total iron binding capacity. In certain embodiments, the complex is at 50% iron binding capacity or less, such as at about 50%, 40%, 30%, 20%, 10%, 5%, or 1% iron binding capacity. In one embodiment, the complex can be at about 0% iron binding capacity (i.e. iron-free ferritin or apoferritin, having 100% or close to 100% iron binding capacity remaining). The H-ferritin can be modified to decrease the likelihood that it will be recognized by any endogenous receptors or to increase excretion by the body. Such modifications are well within the expertise of someone practiced in the art and these modifications need not impact the ability of the protein to bind iron. The multi-subunit ferritin complexes suitable for use as iron chelators comprise H-ferritin subunits, but can also comprise some L-ferritin subunits. In certain embodiments, the multi-subunit ferritin complex comprises at least 20% H-ferritin as compared to L-ferritin, such as about 20%, 30%, 40%, 50%, 60%, 70%, 80%, 90%, or 100% H-ferritin as compared to L-ferritin.

The delivery of the multi-subunit ferritin complex for use as an iron chelator can include the same range of delivery mechanisms (i.e. targeting moieties and/or liposomes or other vesicles) as described elsewhere in this application for delivery of ferritin-iron complexes to treat iron deficiency disorders. The multi-subunit ferritin complex can delivered to the gastrointestinal tract, within the cells lining the gastrointestinal tract (where it could be taken up but not enter the blood stream), or within the blood itself where it would compete effectively for non-transferrin and possibly even transferring-bound iron. Utilizing this approach, iron that would otherwise inappropriately gain access to the brain in an unregulated manner would be eliminated. Furthermore, chelating iron from the blood and systemic organs would promote a redistribution of iron within the body including release of iron from the brain. In some cases, apoferritin or ferritin complexes at less than 100% of total iron binding capacity can be delivered directly into the cerebrospinal fluid to stimulate iron release from the brain.

Ferritin has the capacity to bind not only iron but also a range of metals many of which are toxic to the body. Thus another embodiment of this invention relates to use of apoferritin (or other multi-subunit ferritin complexes at less than 100% of total iron binding capacity) to reduce and eliminate potentially toxic metals from the gastrointestinal system, the blood, the brain and the body in general. Thus it is possible for apoferritin to be utilized as a general metal cleanser for blood.

In blood transfusions, at least 15% of cells will lyse during the infusion process, releasing potentially damaging free iron. The transfusions are performed on patients who need red blood cells (RBCs) and thus are anemic. The present invention relates to a method for mixing apoferritin (or other multi-subunit ferritin complexes at less than 100% of total iron binding capacity) in with the transfusate, which not only provides a chelator for the iron released due to cell lysis but also serves to make that iron available to the body in a more physiological or bioavailable form. One patient population that requires frequent transfusions includes patients with thalessima. This population eventually suffers from liver damage due to excessive iron accumulation. H-ferritin and/or multi-subunit ferritin complexes comprising H-ferritin can help distribute the iron more effectively in the body thus limiting excessive accumulation in the liver. Another population receiving frequent blood transfusions are neonates and especially premies. Providing H-ferritin, multi-subunit ferritin complexes comprising H-ferritin, and/or ferritin-iron complexes with the transfusate would improve iron distribution including iron distribution to the brain for brain development.

The ferritin subunits, including H-ferritin subunits, can be expressed in the body of the patient. In this embodiment, the ferritin-iron complex would form in vivo. A number of plasmid carriers and transfection reagent systems are available to transfect cells ex vivo in order to generate either stable transformants or transiently transfected cells for reinfusion into the host animal or patient. Suitable expression plasmids are commercially available as are transfection reagents, many of the latter being cationic liposomes of one type or another. For in vivo as well as ex vivo gene transfer, such as gene therapy, suitable vectors are known in the art and include retroviral vectors, adenoviral vectors, adeno-associated viral vectors, lentiviral vectors, and electroporation systems.

Other aspects and advantages of the present invention will be understood upon consideration of the following illustrative examples. The examples are not to be construed in any way as limiting the scope of this invention. Those of skill in the art should, in light of the present disclosure, appreciate that changes can be made in the specific embodiments which are disclosed and still obtain a like or similar result without departing from the spirit and scope of the invention.

All references, publications and patent documents cited in this application are incorporated by reference herein. By their citation of various references in this document, Applicants do not admit any particular reference is "prior art" to their invention.

EXAMPLES

Example 1

Ferritin Preparation

All the experiments in this example used recombinant human H-ferritin or horse spleen ferritin. The recombinant human H-ferritin was prepared by transforming chemically competent Br21 cells with a His tagged recombinant human H ferritin plasmid. After the cells were grown, the protein was purified with a nickel protein filter column to a final concentration of 2.8 mg/ml. The horse spleen ferritin was obtained commercially (Sigma), and was chosen because it contains about 90:10 L to H ferritin subunits.

Cell Culture and Preparation of Endothelial Cell Monolayer

We used bovine retinal endothelial cells (BRECs) as an in vitro model of the blood brain barrier (BBB) in order to test the hypothesis that ferritin can be transported across a layer of endothelial cells and to begin to address the mechanism of ferritin transport across the BBB. This well studied model has been shown to posses all of the necessary characteristics and attributes of a blood-neural barrier (Antonetti D. A., et al. *J. Neurochem.* 80: 667-677, 2002). Cow eyes were obtained from a local abattoir and the bovine retinal endothelial cells (BRECs) were isolated and processed according to a previously published procedure (Gardiner T. A., et al. *Lab Invest.* 72: 439-444, 1995). BRECs were grown in MCDB-131 media (Sigma, St. Louis, Mo., USA) supplemented with 10% FBS, 10 ng/mL EGF, 0.2 mg/mL ENDO GRO™ (VEC Technologies, Inc., Rensselaer, N.Y., USA), 0.09 mg/ml Heparin, antibiotic/antimycotic solution (Gibco, Rockville, Md., USA), and Tylosin antibiotic (Sigma). The cells are initially cultured in flasks until they reached at least 80% confluence. Subsequently, the BRECSs were gently trypsinized and grown to confluence on COSTAR® TRANSWELL™ 0.4 μm porous filters (Coming, Acton Mass.). Fibronectin was added at a concentration of 1 μg/cm$^2$ to promote adherence to the filter. The cells were then washed and stepped to serum-free EGF-free MCDB-131 media supplemented with 100 nm hydrocortisone for 72 hours. The addition of hydrocortisone to these cell cultures promoted the formation of tight junctions.

Ferritin Transport in the BBB Model

Pre-purified transferrin was purchased and resuspended to a final concentration of 2.5 mg/ml. About 250 μg of recombinant human H ferritin, horse spleen ferritin (Sigma) and transferrin were labeled with Fluorescein isothiocyanate (FITC) (Pierce Biotechnology) in 100 mM carbonate/bicarbonate buffer, pH 9.0. Removal of excess or hydrolyzed FITC was achieved by passage through a 5-ml G-25 desalting column. The FITC conjugated H-ferritin, spleen ferritin, and transferrin were concentrated and buffer was exchanged with PBS in a CENTRIPREP® concentrator (Amicon, Inc., 10,000 MWCO). Transferrin was included as a positive transport control in the BREC model (Burdo J. R., et al. *Neuroscience* 121: 883-890, 2003).

Rate of flux across confluent BREC monolayer was determined as described previously in Burdo et al., 2003 with some modifications using the equation: $(Bf/Tf)*(Vb/A)=(Flux)*t$. Briefly, BRECs were grown to confluence in transwell apparatus before adding 140 μg of either FITC-labeled rH-ferritin, spleen-ferritin, or transferrin to the top chamber (apical). Transport of the tracer is determined by sampling from 100 μl aliquots from the bottom chamber (basal) collected at various times (15, 30, 45, 60, 120, 180, and 240 min) following addition of the tracer to the apical chamber. The aliquots from the basal chamber are then analyzed for fluorescence in a spectro-fluorometer (SPECTRAMAX® GEMINI, Molecular Devices). The rate of flux is obtained as the slope (cm/s) from the plots of bottom chamber fluorescence per unit amount of top chamber fluorescence (Bf/Tf) versus time (t). Here, Bf, indicative of the amount of tracer transported across the monolayer, is normalized to the volume of the basal chamber (Vb) and also the surface area available for transport (A). The concentration of Tf in the top chamber does not change significantly over the 4 hours that the experiment is performed, thus is considered constant for calculating flux. The amount of fluorescence in the top chamber is obtained from a 100 µl aliquot at the end of the transport assay (4 h).

As a control for paracellular flux, RITC dextran (70 kDa) was added simultaneously to the apical chamber as a control. Dextran is not taken up at an appreciable level by endothelial cells (Raub T. J., et al. *J. Cell Physiol.* 149: 141-151, 1991). Thus, any accumulation of dextran in the basal chamber would be due to paracellular transport. None of the conditions affected the rate of flux of dextran which was minimal in each condition.

Determination of Transport Mechanism

To determine if pinocytosis contributed significantly to the transport of ferritin, 50 µg/ml of filipin was added to the apical chambers of the transwell apparatus for 30 minutes before the ferritin and dextran were added. The addition of filipin has been shown to inhibit the action of nonspecific transport via pinocytosis (Stremmel W, et al. *Lipids* 36: 981-989, 2001). To determine if H-ferritin uptake occurs via clathrin-dependent endocytosis, studies were performed in potassium deficient medium (100 mM NaCl/50 mM HEPES). The cells were incubated in potassium deficient medium for 10 minutes before the addition of ferritin. Intracellular potassium depletion inhibits receptor-mediated endocytic processes occurring through clathrin-coated pits. These latter experiments could only be performed for one hour before the potassium depletion altered the integrity of the cell to cell junctions as indicated by an increase in dextran transport. Each treatment condition (or standard) was performed a minimum of six times. Throughout the experiments the cultures were visually assessed to assure that the experimental treatments and manipulations did not affect cell viability. As in the baseline experiments, dextran labeled RITC was included as an indicator of the integrity of the tight junctions. Differences between the means for FITC H-ferritin under the different conditions were analyzed using one-way analysis of variance. For those measurements with significantly different means, a Bonferroni post hoc comparison was done to analyze pairwise differences. The level of significance was set at $p<0.05$.

Binding Experiments

Saturation analysis: The binding experiments on BREC cell homogenates were performed in duplicate on the fourth passage of the BREC cells using $^{125}$I-recombinant human H-ferritin or horse spleen ferritin. The specific activity for both was ~340,000 cpm/pmol. To establish the total, specific and non-specific binding a range of concentrations of $^{125}$I-H-ferritin was added with or without 1000 fold molar excess of unlabeled H-ferritin to 100 µg total protein of the BREC cell homogenate. The binding buffer consisted of 50 mM Tris-HCl (pH 7.4), 0.1% BSA. Incubations were carried out at 22° C. for 2 h. The binding was terminated by the addition of 3 ml of ice-cold 50 mM Tris-HCl. Using a cell harvester, the bound radioactivity was isolated by rapid filtration and washing over Whatman glass fiber C filters, which were previously coated with 5% non-fat dry milk and 0.1 mg/ml horse spleen ferritin.

Equilibrium competition binding assays were performed, where the increasing concentration of unlabeled H-ferritin was incubated with 25 µg of protein of BREC homogenate at 22° C. with 0.4 nM $^{125}$I-H-ferritin for 120 minutes in the same binding buffer described before. Termination of binding, isolation of membranes and calculations of specific binding were performed as described above.

Rat Brain Microvasculature

Microvessel preparation: Six adult rats were used for each microvessel preparation. The rats were anesthetized with a lethal dose of sodium pentobarbital (100 mg/kg body weight) and then decapitated. The brain was removed and placed in a petri dish on ice. The cerebellum and the meninges were removed and 5 volumes of Microvascular buffer (1×MVB-1× salt, 1×HEPES, 0.5% BSA and 5 mM glucose) was added with protease inhibitors. The brains were gently homogenized with 20 strokes using a glass-teflon homogenizer (0.25 mm clearance) and the homogenate centrifuged at 1000×G for 10 minutes at 4° C. The supernatant was discarded and the pellet resuspended in 5 volumes/rat of 17% Dextran (1:1 ratio of 1× salt and 1×HEPES with dextran) followed by vortexing and then centrifugation at 3000×G at 4° C. The microvessels are collected from the wall of the tube and resuspended in 20 ml of 1×MVB buffer. The microvessels were filtered through a 120µ mesh. Then the microvessel preparation was further purified by adherence to glass beads (Sigma) supported on a 40µ mesh. The beads were washed with buffer that has protease inhibitors added. The beads were rinsed in 5 ml of MVB and then the microvessels were pelleted by centrifuging at 1000×G at 4° C. for 15 minutes. The microvessels were resuspended in 1 ml of HES+ (10 mM HEPES, 1 mM EDTA, 250 mM sucrose, pH 7.4 and protease inhibitor cocktail) (Sigma) and a total protein concentration determined. The samples were stored at −80° C. until use.

Ferritin Binding on Microvessels

The binding suspension consisted of 50 mM Tris-HCl (pH 7.4), 0.1% BSA, and 20 µg of membrane protein preparation with or without the addition of 1 µM unlabeled H-ferritin in a final volume of 250 µl. Binding was terminated by the addition of 3 ml of ice-cold 50 mM Tris-HCl. Bound radioactivity was isolated by rapid filtration over Whatman glass-fiber C filters that had been previously coated in a solution of 5% nonfat dried milk (Blotto) with 0.1 mg/ml spleen ferritin. This combination was determined empirically to reduce the nonspecific binding of radiolabeled protein to the filters to 1-3% of the total counts added. The filters were washed 5× with 3 ml of ice-cold 50 mM Tris containing 200 mM NaCl. The filters were being counted in a MICROMEDIC 4/200 plus automatic γ-counter. Specific binding was calculated by subtracting binding in the presence of excess unlabeled H-ferritin (nonspecific binding) from binding without excess unlabeled H-ferritin present (total binding).

Saturation Analysis

Each binding experiment was performed in duplicate. Increasing concentrations of $^{125}$I-H-ferritin were added to binding suspensions consisting of the same binding buffer described previously with 20 µg of membrane protein preparation with or without the addition of 1 µM unlabeled H-ferritin in a final volume of 250 µl. After a 120-min incubation at 22° C. binding was terminated, and total, nonspecific, and specific bindings were calculated as described previously.

Competition Assays

Increasing concentrations of unlabeled competitors (H-ferritin and spleen ferritin) were incubated for 60 min at 22° C. with 100 µg of membrane protein in the presence of 0.4 nM $^{125}$I-H-ferritin in the same binding buffer described previously. Binding, termination of binding, isolation of membranes, and calculations of specific binding were performed as described above. The competition experiments were performed in duplicate.

In Vivo Uptake Studies

H and spleen ferritin (1.2 mg) were incubated in 40 µl 1 mM nitriolotriacetic acid (pH 6.0), 0.5 µl ferrous ammonium sulfate, 2 µl 0.5M sodium bicarbonate, and 40 µC of $^{59}$FeCl for 4 hours at 37° C. After incubation, ferritin was dialyzed in a 10,000 MW cartridge in 1×PBS for 24 hours to remove any unbound $^{59}$Fe. The specific activity was 0.04 µC/g for H-ferritin and 0.08 µC/g for spleen ferritin. Radiolabeled protein (3.4 µg/gram wt) was injected (n=3) into the tail vein of female Sprague-Dawley rats (~350 g). After 48 hrs, the rats were decapitated and the organs removed immediately. Each organ was dissected and rinsed thoroughly in 0.1M PBS. For the brain, the cerebrum was removed from the cerebellum and bisected and the meninges were dissected clear of the brain. One gram of tissue (wet weight) from each organ was used to determine the iron uptake.

H-ferritin deficient mice were evaluated as an experimental model to determine if potentially compromised iron management in an organ could influence ferritin iron delivery. A similar approach was used to investigate ferritin uptake in control and H-ferritin deficient mice as described above for the rats except that the mice were injected intraperitoneally. The specific activity for the H-ferritin was 0.06 µC/g and for the spleen ferritin was 0.31 µC/g. Ferritin was injected and allowed to circulate in the bloodstream for 48 hours until the mice were killed and the organs removed.

The amount of radioactivity in each organ was determined on a sodium iodide (NaI) based, single channel analyzer well counter system (Can berra Industries Inc.) for one minute. The gamma counts/min (cpm) were subtracted from background counts, divided by the efficiency of the counter, and then divided by the disintegration counts/min to calculate µC. To calculate % total, organ µC was divided by total µC injected then multiplied by 100%.

Results

In vivo uptake of ferritin: The possibility that iron bound to ferritin could be taken up by different organs in rats was determined by injecting H or spleen ferritin containing radiolabeled $^{59}$Fe into the tail vein of adult rats. The uptake of iron from H-ferritin was significantly greater than that for spleen ferritin in the brain, heart, kidney, muscle and lung (FIG. 1A). The amount of $^{59}$Fe was 2× higher in the brain when it was presented bound to H-ferritin than with spleen ferritin (p<0.005) (FIG. 1B). Only the liver, had significantly higher uptake of iron from Spleen ferritin compared to H-ferritin (p<0.05).

To determine the influence of potential alterations in iron storage capacity within various organs on H and spleen ferritin delivery of iron to various organs, we investigated the uptake of $^{59}$Fe from these proteins in a mouse line that is deficient in H-ferritin (Thompson K. J., Fried M. G., Zheng Y., Boyer P., Connor J. R. J Cell Sci. 115: 2165-2177, 2002). Iron delivery by H-ferritin was decreased in the spleen, lung and muscle (p<0.05) in the H-ferritin compromised mice compared to littermate controls (FIG. 2A). A similar finding was observed in brain (FIG. 2B). Spleen ferritin uptake was unaltered in any organ in the iron storage compromised mice (FIGS. 3A and 3B).

Transport of Ferritin: Although serum ferritin could have unrestricted access to systemic organs, in order to be effective for delivering iron to the brain it would have to cross an endothelial cell barrier (BBB). To begin to investigate the possibility that ferritin transcytosis was possible, we utilized a cell culture model of the BBB. H-ferritin but not spleen ferritin was transported across the BREC cell monolayer in significant amounts (FIG. 4). The rate of FITC-labeled H-ferritin that was transported across the BREC monolayer was 5× more than the RITC-labeled dextran (p<0.001). The rate of transport of spleen ferritin was similar to the level seen in the dextran control. To determine the mechanism by which H-ferritin is transcytosed we performed the transport assays in a potassium free medium to block the formation of clathrin coated vesicles. The absence of clathrin coat formation was associated with an 80% (p<0.001) decrease in the rate of H-ferritin transport. In contrast, filipin pretreatment of the BRECs, to block pinocytosis, resulted in no significant decrease in rate. A dextran control was included include in each experimental condition and the rate did not change from that shown in the graph for the untreated condition (data not shown). Transferrin transport was included as a positive control and was detected as previously reported (Burdo J. R., Antonetti D. A., Wolpert E. B., Connor J. R. *Neuroscience* 121: 883-890, 2003). The specific activities of fluorescently labeled transferrin and ferritin were different so no conclusions can be made about the relative rates of transport for these two proteins.

Ferritin Binding Analysis: To more thoroughly evaluate the mechanism of iron delivery via ferritin the brain, binding studies were performed to determine if the transport of ferritin in the BREC model was receptor mediated. In addition, to expand the evaluation of ferritin binding to an in vivo system, microvasculature was isolated from rat brains (RBMVs). Ferritin binding to BREC and RBMVs was performed utilizing a saturation experiment as well as a competition experiment. $K_d$ and $B_{max}$ values were obtained from both the approaches using non-linear regression in GRAPHPAD PRISM® 4.0 (GraphPad Software, Inc.).

Saturation Curves: Various concentrations (1, 2, 3, 5, 7, and 10 nM) of $^{125}$I labeled ferritin (rH-ferritin or spleen ferritin) were incubated with 100 µg of the tissue (BRECs or RBMVs). Total and non-specific binding (in presence of 1000 nM unlabeled ferritin) were obtained by performing the assay on Whatmann filters. To obtain the $K_d$ and $B_{max}$ from such a binding assay, non-linear global regression for one-site binding was performed. In this method, both total and non-specific binding were plotted against the concentration of labeled ferritin. The resulting plots were fitted to the equations: Nonspecific=NS*X and Total=Specific+Nonspecific. Where, Specific=Bmax*X/($K_d$+X). In the global approach, specific binding is not derived from the total and nonspecific binding data. Instead the values of $K_d$ and $B_{max}$ are obtained by sharing the non-specific binding constant (NS) between the two data sets (total and nonspecific). The data from this regression analysis are shown in FIGS. 5A and 5B. Only the rH-ferritin has significant saturable binding to either the BRECs or the RBMVs. The $K_d$ and $B_{max}$ for the RBMVs are 7.9±1.6 nM and 572.6±64.0 fmol/mg protein respectively. For the BRECs, the $K_d$ is 2.7±0.9 nM and the Bmax is 465.7±63.1 fmol/mg protein. The R2 value for the curve fit is >0.8 for both BRECs and RBMVs.

Competition Curves: Various concentrations of cold ferritin (0.03, 0.1, 0.3, 1, 3, 10, 30, 100, 300, and 1000 nM) were incubated with 100 µg of BRECs or RBMV tissue along with 0.4 nM of radiolabeled ferritin. Total binding was obtained by performing the assay on Whatmann filters. The total binding (fmol/mg protein) was then plotted against log [concentration (nM)]. These plots were then fit to the one-site competition equation: Total=Bottom+(Top−Bottom)/(1+10 (X−LogEC$_{50}$)). This data are shown in FIGS. 6A and 6B. The results show that H-ferritin can effectively compete for the binding sites, but not spleen ferritin. Determining the $K_d$ and $B_{max}$ from the competition curves for the BRECs resulted in $K_d$ of 2.0 nM and $B_{max}$ of 235.1 fmol/mg protein. The corresponding values for RBMVs are $K_d$=3.4 nM and $B_{max}$=304.6 fmol/mg protein. The R2 value for the fit is >0.95 for both BRECs and RBMVs. The values generated by the two different curves are within acceptable ranges.

Discussion: The results of this study reveal that ferritin can deliver iron to multiple organs including the brain. Furthermore, the amount of iron delivered by ferritin is enhanced when the iron is delivered via H-ferritin instead of L-ferritin for most organs except the liver. The amount of H-ferritin iron that is taken up by cells can be altered when iron storage capacity is compromised; as demonstrated in the H-ferritin deficient mice, whereas iron delivery by L-ferritin is not significantly affected in this model. These latter results suggest a feedback system for H-ferritin. Thus we have identified a novel transport system for iron delivery to the brain and one that could be highly significant given the amount of iron (up to 4500 Fe atoms) that can be housed in a single molecule of ferritin compared to transferrin (maximum of 2 Fe atoms). The identification of a non-transferrin dependent iron delivery system to the brain is consistent with our previous reports showing iron delivery to the brain in the absence of serum transferrin (Malecki E. A., Devenyi A. G., Beard J. L., Connor J. R. *J Neurosci Res.* 56: 113-122, 1999). This study also adds to the continuing quest for the existence of a ferritin receptor. Ferritin receptors have been reportedly demonstrated on hepatocytes (Mack U., et al. *J Biol. Chem* 258: 4672-4675, 1983), although saturation was not demonstrated in this model and in the brain (Hulet S. W., Heyliger S. O., Powers S., Connor J. R. *J. Neurosci Res.* 61: 52-60, 2000). A protein has been recently identified as the putative ferritin receptor (Chen T. T., et al. *J Exp Med.* 202: 955-65, 2005).

In the brain, in addition to binding to a receptor, ferritin must be transcytosed across the BBB. In this study, we demonstrated that ferritin can be transported across a cell culture model of the BBB. The transport of ferritin in this cell culture model is clathrin dependent and receptor mediated and strongly favors the H-subunit. The preference for H-ferritin binding is consistent with the transport data. Binding of ferritin is also demonstrated on microvasculature from the rat brain and this binding, similar to the cell culture model, also strongly favored the H-subunit. The binding and transport data are consistent with the iron uptake data that revealed increased delivery to the brain if the iron was associated with H-ferritin relative to spleen (L-rich) ferritin. The uptake of ferritin, the differences in iron delivery between H and L ferritin and the changes in H-ferritin uptake in the H-ferritin compromised mice all suggest the possibility of a ferritin receptor and binding for H-ferritin was directly demonstrated on two different sources of endothelial cells.

The data suggesting that the mechanism by which ferritin is transported across the BBB is clathrin dependent and not pinocytosed is similar to that previously identified using the same system for transferrin (Burdo J. R., Antonetti D. A., Wolpert E. B., Connor J. R. Mechanisms and regulation of transferrin and iron transport in a model blood-brain barrier system. *Neurosci.* 121: 883-890, 2003). The mechanism for iron delivery to the brain and regulation of those mechanisms is central to understanding how iron may accumulate or fail to reach normal levels and thus underlie or contribute to a variety of neurological disorders (Zecca L, Youdim M B, Riederer P, Connor J R, Crichton R R. *Nat Rev Neurosci.* 5: 863-873, 2004). The studies of transcytosis of iron bound to transferrin have provided conflicting results. Some studies show that iron entering the brain is bound to transferrin and other studies show iron transport that is not associated with transferrin. We have provided evidence that there are both transferrin and non-transferrin dependent systems for iron delivery to the brain and that the preference for one pathway over another appears to be dependent on the iron status of the endothelial cells. The iron status of the endothelial cells forming the BBB and how this iron status impacts on the regulation of transferrin receptors for transferrin mediated uptake of iron has been largely ignored in studies on the mechanisms of brain iron uptake (see Burdo and Connor 2003 for review). The expression of transferrin receptors in cells is well known to be regulated by the intracellular iron status of the cell (Aisen P., et al. *Int J Biochem Cell Biol.* 33: 940-959, 2001) and endothelial cells have the same iron regulatory mechanism for transferrin receptors as other cells (Georgieff M. K., et al. *J Pediatr.* 141: 405-9, 2002). Endothelial cells of the brain also express the divalent metal transport protein whose function is to mediate iron release from endosomes within the cell and contain relatively high amounts of ferritin indicating the existence of iron stores. The concept that brain endothelial cells have their own considerable iron requirement and regulate their own iron uptake is consistent with the high concentration of mitochondria in these cells and thus high iron requirement. Therefore, at least some of the iron delivered to these cells by transferrin should be retained within the endothelial cells. The mechanism by which iron is released from ferritin is not well understood and some have proposed that degradation of ferritin is required to release iron. Therefore ferritin may be more likely to be transcytosed with a high amount of its iron content intact and may be less likely to share its iron with endothelial cells than transferrin. The mechanism for regulating ferritin delivered iron to the brain is unknown at this time, but the decrease in H-ferritin delivered iron in the H-ferritin deficient mice strongly suggests that such a regulatory mechanism exists.

Although the function of ferritin as an iron storage protein is well established, the concept that H— ferritin could be actively secreted by cells and possibly deliver iron has not been previously studied. Ferritin levels in the blood fluctuate widely under even normal conditions. Ferritin mRNA is bound to polyribosomes that are attached to the endoplasmic reticulum in rat liver cells which would support a secretory pathway for ferritin. Direct secretion of ferritin (both subunits) has been demonstrated in differentiated rat hepatoma cells and the release of H-ferritin but not L-ferritin from microglial cells in culture has been shown (Zhang X., Surguladze N., Slagle-Webb B., Cozzi A., Connor J. R. *Glia* 54: 795-804, 2006).

The source of ferritin for the receptors on the BBB and other organs is presumably from the serum. The presence of ferritin in the serum is well established, but serum ferritin is traditionally considered to be predominantly made of the L-subunits. The source of this L-rich serum ferritin is primarily from lysed macrophages (McGowan S. E., et al. *J. Lab Clin. Med.* 111: 611-617, 1988). We have surprisingly shown, however, that the binding of ferritin, transport of ferritin and delivery of iron to the brain all strongly favor H-rich ferritin. Thus the physiological significance of our finding based on the relatively small amounts of H-ferritin in the serum suggests that ferritin could be secondary to transferrin as a source of iron for the brain. It must be remembered, however, that a mol of ferritin can deliver 2000× more times the iron than a mol of transferrin.

Furthermore, there are conditions under which H-ferritin is elevated in the plasma such as inflammation and in association with some cancers (Elliott R. L., et al. *Breast Cancer Res. Treat.* 30: 305-309, 1994). Therefore, chronic inflammatory conditions could increase brain iron status, a concept consistent with iron accumulation in a number of neurodegenerative diseases including Alzheimer's and Parkinson's Diseases.

Example 2

Introduction

We have developed a novel dietary approach to alleviating iron deficiency. This approach stemmed from our discovery of receptors for H-ferritin in the body, including the brain, and demonstration that H-ferritin is the preferred manner of iron uptake relative to L-rich ferritin into all organs except for the liver. Others have shown that H-ferritin is enriched in breast milk suggesting this protein is the mechanism for iron delivery between mother and infant. This latter statement is potentially true for all mammals and not just humans. Furthermore H-ferritin gene sequence and protein structure is highly conserved in the animal kingdom. Thus, the application of H-ferritin as an iron delivery protein should not be limited to humans.

Figure 8:
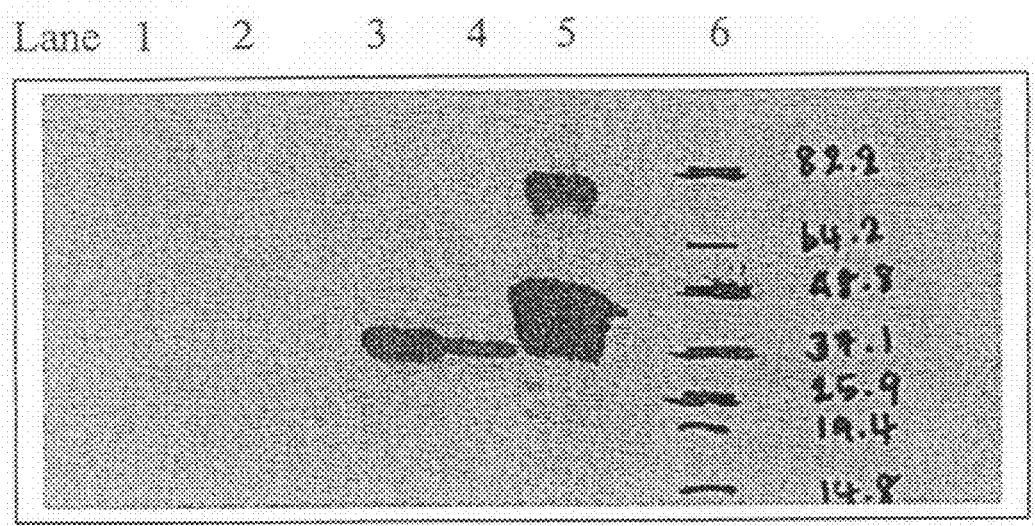
FIG. 8 is a Western blot. The proteins were first separated by gel electrophoresis and then the gel was stained with the Perl's reaction, a stand histological stain for iron that has been used to demonstrate iron content of ferritin. Lanes 1 and 2 are from yeast colonies that had been transformed with L-ferritin. No reaction product for iron is seen in these lanes. Lanes 3 and 4 are protein extracts from yeast expressing H-ferritin under normal iron media conditions (Lane 4) and iron enriched media (Lane 3). An H-ferritin standard was used as a control (lane 5). Lane 6 contains molecular weight markers to indicate the size of ferritin.

We have devised a mechanism for delivering H-ferritin as a dietary supplement using yeast. To begin this approach, the first study was to transform yeast to express the human H-ferritin gene which can be translated into the H-ferritin protein. The immunoblot shown in FIG. 7 demonstrates that H-ferritin is expressed by the yeast and there is no cross reaction with L-ferritin. The second study was to demonstrate that enriching the media in which the yeast were growing with ferrous iron sulfate would increase the iron content of the ferritin that they were expressing. These results are shown in FIG. 8.

Feeding Studies

Figure 9:
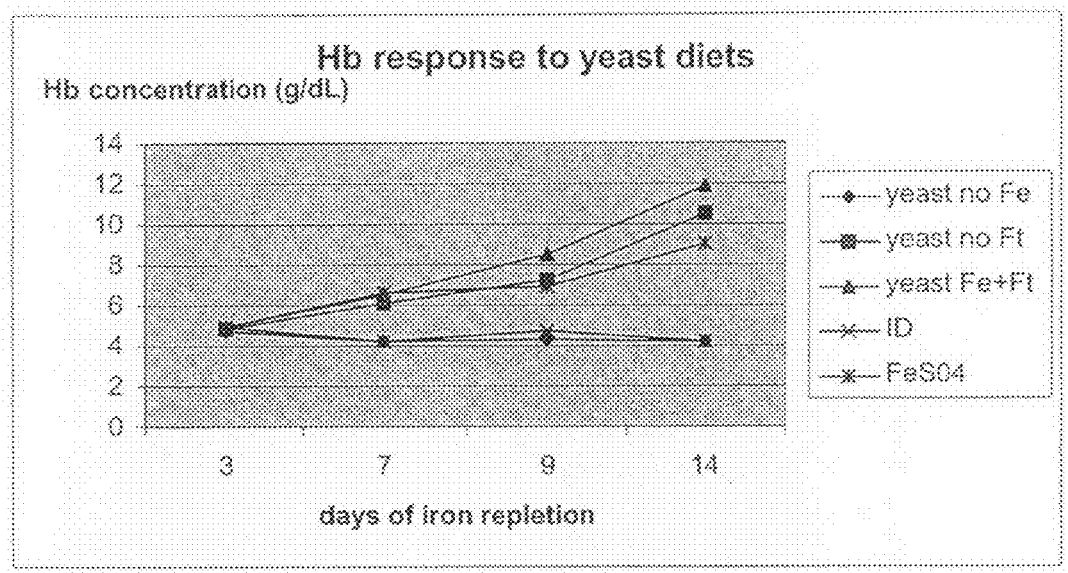
FIG. 9 shows results obtained using a standard rat model of iron deficiency. The animals on an iron deficient (ID) diet had the lowest levels of Hemoglobin (Hb). The animals that received yeast without iron (yeast no Fe) had Hb levels similar to the ID animals. Improvements in the Hb levels were seen in the other three groups with the most rapid increase in improvement occurring in the animals that received the yeast that were iron supplemented and fortified with ferritin (ft). Even the animals receiving iron supplemented yeast without ferritin had Hb levels that improved more than the $FeSO_4$ group.

To test the efficacy of ferritin fortified yeast as a model for treating iron deficiency, we used a standard rat model of iron deficiency. Rat pups were nursed by iron deficient dams until weaning at 25 days of age. Upon weaning the animals were assigned to one of five groups. Group 1: maintained on iron deficient diet (ID). Group 2: fed a standard iron replenishment diet of 35 mg/kg of FeSO4, Group 3: fed a diet that contained yeast that had not been supplemented with iron (yeast no Fe). Group 4: fed a diet that included yeast that had been iron supplemented but not fortified with H-ferritin (yeast no Ft), Group 5: yeast that had been transformed with H-ferritin and supplemented with iron (yeast Fe+Ft). Blood samples were collected from these animals at 3, 7, 9 and 14 days after weaning. The results are shown in FIG. 9. The animals continuing on the ID diet had the lowest levels of Hemoglobin (Hb). The animals that received the yeast without iron had Hb levels similar to the ID animals. Improvements in the Hb levels were seen in the other three groups with the most rapid increase in improvement occurring in the animals that received the yeast that were iron supplemented and fortified with ferritin. Even the animals receiving iron supplemented yeast without ferritin had Hb levels that improved more than the $FeSO_4$ group.

Figure 10:
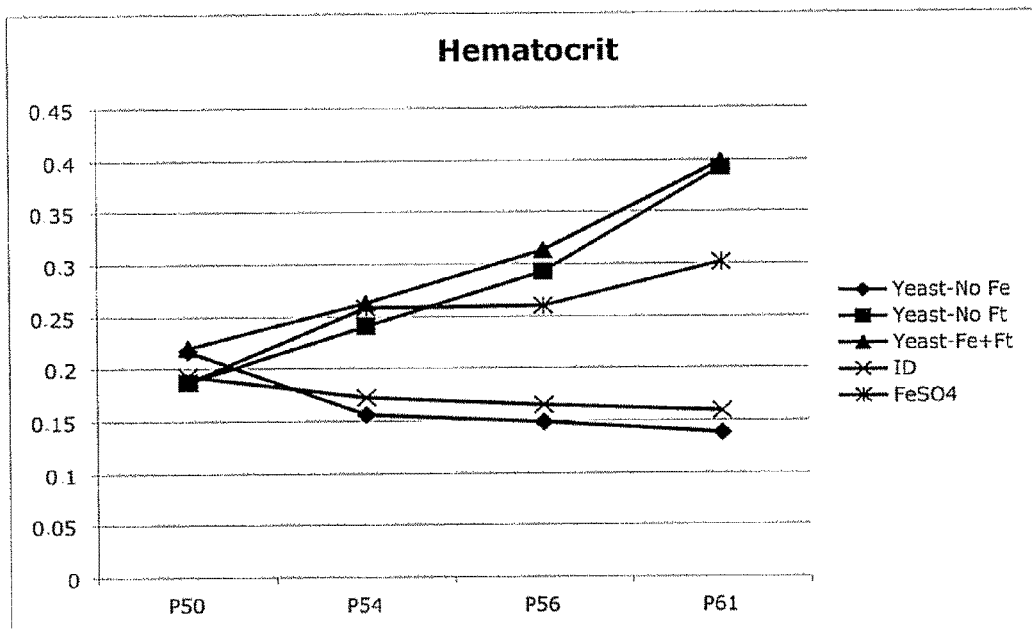
FIG. 10 represents hematocrit levels from the group of animals tested in FIG. 9. These data show that yeast as a vehicle for iron are equally effective at correcting the hematocrit in the presence or absence of H-ferritin and both are significantly better than the standard current treatment option, $FeSO_4$. Animals who were continued on the ID diet and those receiving yeast that had not been iron supplemented showed no increase in hematocrit over the 11 days examined.

Hematocrit levels were also monitored in the same group of animals. These data are shown in FIG. 10. These data show that yeast as a vehicle for iron are equally effective at correcting the hematocrit in the presence or absence of H-ferritin and both are significantly better than the standard current treatment option, $FeSO_4$. Animals who were continued on the ID diet and those receiving yeast that had not been iron supplemented showed no increase in hematocrit over the 11 days examined.

Figure 11:
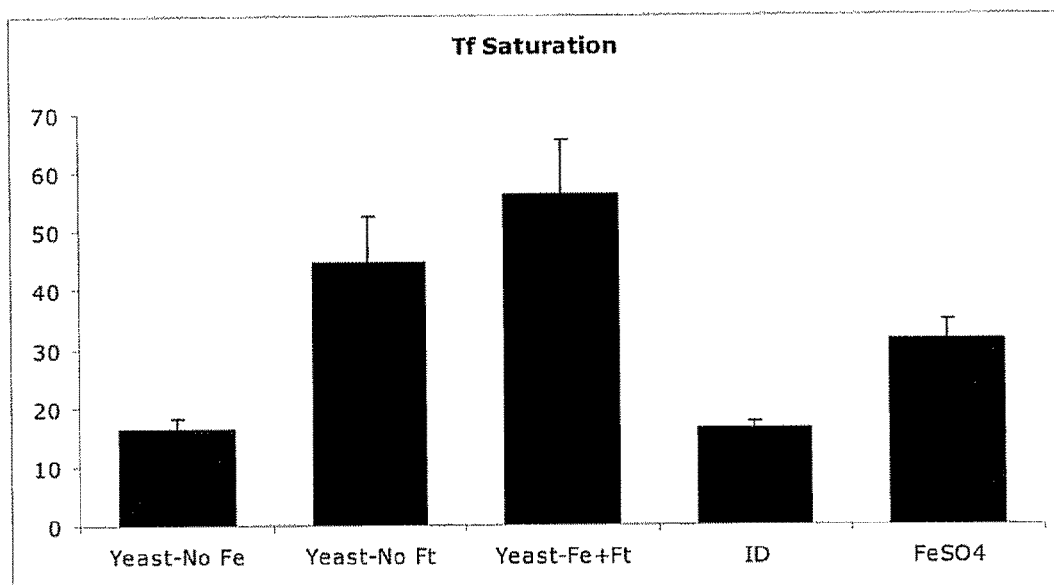
FIG. 11 shows the results of a test measuring iron mobilization in the group of animals tested in FIGS. 9 and 10. These data show that the ferritin fortified iron enriched yeast (Yeast-Fe+Ft) provided the greatest increase in transferrin (Tf) saturation, followed by the iron enriched yeast without ferritin (Yeast-No Ft).

An important analysis that shows the ability of the body to mobilize the iron, perhaps indirectly a measure of iron bioavailability is transferrin saturation levels. Transferrin is the main iron mobilization protein and is found in serum in high concentrations. The amount of transferrin saturation fluctuates from a normal high of 30% to less than 10% in conditions of anemia. The analysis of transferrin saturation in the animal model we used to evaluate the efficacy of ferritin fortified iron enriched yeast is shown in FIG. 11. In this Figure, it can be seen that the ferritin fortified iron enriched yeast resulted in the greatest increase in transferrin (Tf) saturation followed by the iron enriched yeast without ferritin. This study once again demonstrates the superiority of the yeast as an iron delivery vehicle to $FeSO_4$ in the diet. Animals maintained on the ID diet or fed the control yeast (none iron or ferritin enriched) had the lowest Tf saturations.

Effects on Brain Iron

Figure 12:
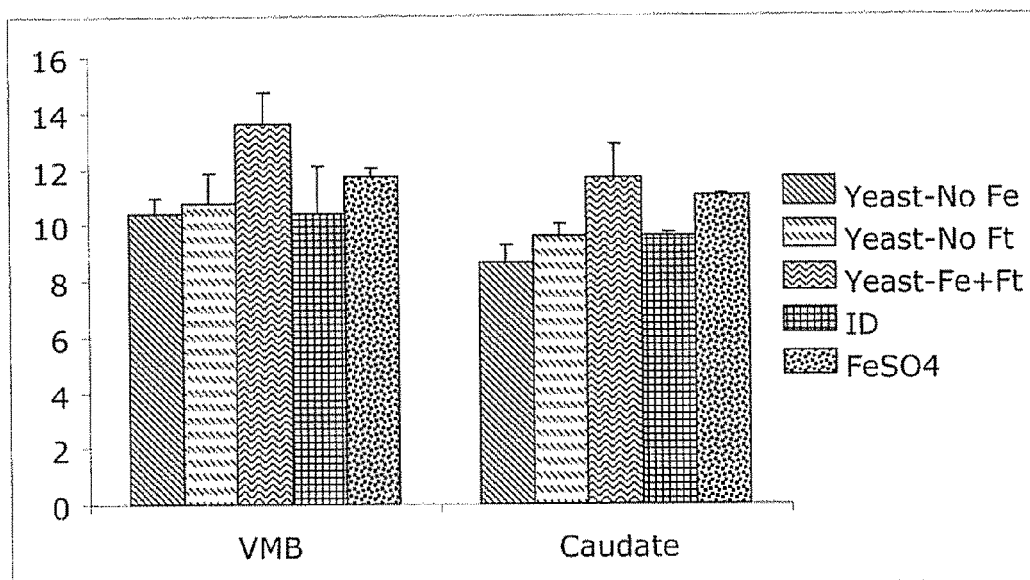
FIG. 12 shows the iron status of two developmentally important areas of the brain, the ventral midbrain and the caudate. The animals described in the Hb and Hct analyses (FIGS. 9 and 10) were killed at 14 days of age and the iron concentration of the ventral midbrain (VBM) and the caudate was determined. The animals receiving the yeast that had been fortified with ferritin and supplemented with iron (Yeast-Fe+Ft) had more iron in both brain regions than any other group.

Because iron deficiency has a significant impact on brain development, the iron status of specific brain regions was monitored in the animals receiving the different diets. In FIG. 12, the iron status of two developmentally important areas of the brain, the ventral midbrain and the caudate is shown. These areas are destined to become relatively iron enriched as the animal (e.g. human) matures. These brain regions are involved in regulation of motor activity; hence the impairment of motor skills in iron deficiency especially when the deficiency occurs during development. The same animals described in the Hb and Hct analyses were killed at 14 days of age and the iron concentration of the ventral midbrain (VBM) and the caudate was measured. The animals receiving the yeast that had been fortified with ferritin and supplemented with iron had more in both brain regions than any other group. This exciting novel finding indicates that the ferritin fortified dietary supplement may be a mechanism to limit neurological deficits associated with iron deficiency. This observation could have tremendous impact on the war against global iron deficiency not only by increasing general health, but by optimizing neurological function.

Figure 13:
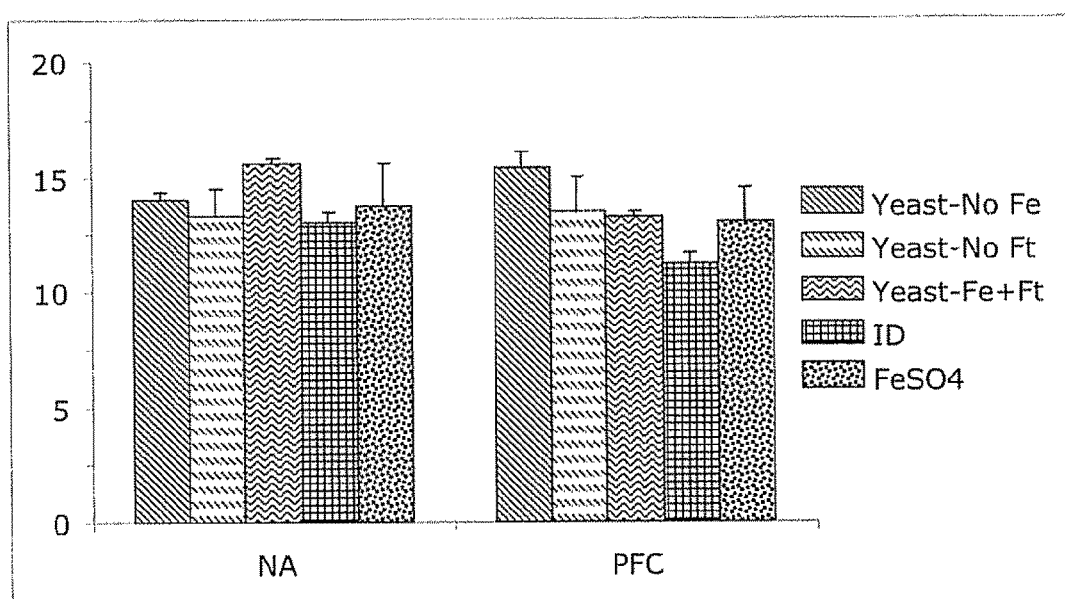
FIG. 13 represents iron levels in the Nucleus Accumbens (NA) and Prefrontal Cortex (PFC) regions of the brain. In this figure, the regional specificity of the iron delivered from the ferritin fortified iron supplemented yeast (Yeast-Fe+Ft) is apparent. In the NA (similar to the VMB and caudate shown in FIG. 12), the iron content is elevated compared to the other modes of iron delivery. In the PFC, however, the iron delivered from the ferritin fortified iron supplemented yeast is similar to that found for the other groups.

To further evaluate regional changes in brain iron status two other areas of the brain, the Nucleus accumbens (NA) and prefrontal cortex (PFC), were interrogated. These results are shown in FIG. 13. In this figure, the regional specificity of the iron delivered from the ferritin fortified iron supplemented yeast is apparent. In the NA, similar to the VMB and caudate shown in FIG. 5, the iron content is elevated compared to the other modes of iron delivery. In the PFC, however, the iron delivered from the ferritin fortified iron supplemented yeast is similar to that found for the other groups. These data suggest that there is a mechanism that regulates the iron delivery from the ferritin fortified iron supplemented yeast in a manner different from the other iron delivery systems and is consistent with our discovery of receptors for H-ferritin on the brain microvasculature.

Summary

The increased iron uptake into the brain and perhaps more importantly, the regional specificity of the uptake, is an unexpected but highly significant finding associated with the present invention. These data suggest that using ferritin fortified iron supplemented yeast should result in improvement of neurological, cognitive and behavioral deficits associated with iron deficiency during postnatal development. The data on hematological parameters are unequivocally strong and indicate that ferritin fortified iron supplemented yeast are a superior mode of dietary iron supplementation.

The invention claimed is:

1. A method for delivering iron to the brain in a patient having an iron deficiency disorder of the brain, comprising administering a ferritin-iron complex to a patient, wherein the ferritin-iron complex comprises human H-ferritin, and wherein a therapeutically effective amount of iron is transported across the blood-brain barrier.

2. The method of claim 1, wherein the ferritin-iron complex comprises recombinant H-ferritin.

3. The method of claim 1, wherein the iron deficiency disorder of the brain is a neurological or neurodegenerative disorder.

4. The method of claim 1, wherein the human H-ferritin-iron complex is administered to the patient by injection, oral, or nasal delivery.

5. The method of claim 1, wherein the patient is a mammal.

* * * * *